United States Patent
Matsuoka et al.

(10) Patent No.: US 7,018,981 B2
(45) Date of Patent: Mar. 28, 2006

(54) CYCLIC MOTILIN RECEPTOR ANTAGONISTS

(75) Inventors: Hiroharu Matsuoka, Shizuoka (JP); Tsutomu Sato, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 515 days.

(21) Appl. No.: 10/362,574

(22) PCT Filed: Aug. 23, 2001

(86) PCT No.: PCT/JP01/07213

§ 371 (c)(1),
(2), (4) Date: Feb. 24, 2003

(87) PCT Pub. No.: WO02/16404

PCT Pub. Date: Feb. 28, 2002

(65) Prior Publication Data

US 2003/0191053 A1    Oct. 9, 2003

(30) Foreign Application Priority Data

Aug. 24, 2000  (JP)  ............... 2000-253950

(51) Int. Cl.
*A61K 38/12*   (2006.01)
*C07K 7/64*    (2006.01)

(52) U.S. Cl. ............... 514/11; 514/9; 514/2; 530/317; 530/300

(58) Field of Classification Search ............... None
See application file for complete search history.

(56) References Cited

U.S. PATENT DOCUMENTS

| 5,972,939 | A | * | 10/1999 | Chen et al. | ............... | 514/237.8 |
| 6,384,031 | B1 | * | 5/2002 | Chen et al. | ............... | 514/237.8 |
| 6,586,630 | B1 | * | 7/2003 | Matsuoka et al. | ............... | 564/153 |
| 2004/0092478 | A1 | * | 5/2004 | Rothermel et al. | ............... | 514/54 |

FOREIGN PATENT DOCUMENTS

| EP | 1 006 122 A1 | 6/2000 |
| JP | 7-138284 | 5/1995 |
| JP | 2000-44595 | 2/2000 |
| WO | WO-00/17231 A | 3/2000 |
| WO | WO-00/44770 A | 8/2000 |
| WO | WO-02/08248 A | 1/2002 |

OTHER PUBLICATIONS

Takanashi H et al "GM-109: A Novel, Selective Motilin Receptor Antagonist in the Smooth Muscle of the Rabbit Small Intesting" Journal o fPharmacology and Expreimental Therapeutics, American Society for Pharmacology and, US, vol. 273, no. 2, (1995), pp:624-628.

Haramura Masayuki et al "Design and synthesis of N-Terminal cyclic motilin partial peptides: A novel pure motilin antagonist" Chemical and Pharmaceutical Bulletin (Tokyo), vol. 49, No. 1, (Jan. 2001) pp: 40-43.

Kazuhiro Momose et al. "Anxiolytic Effect of Motilin and Reversal with GM-109, a Motilin Antagonist. in Mice" Peptieds 19(10) 1739-1742, (1998).

Takio Kitazawa et al. "Functional Characterization of Neural and Smooth Muscle Motilin Receptors in the Chicken Proventriculus and Ileum" *Regulatory Peptieds* 71:87-95. (1997).

Shin Fukudo et al. "Colonic Motility. Autonomic Function, and Gastrointestinal Hormones under Psychological Stress on Irritable Bowel Syndrome" *Tohoku J. Exp. Med.* 151: 373-385 (1987).

D M Preston et al. "Positive Correlation between Symptoms and Circulation Motilin. Pancreatic Polypeptide and Gastrin Concentrations in Functional Bowel Disorders" *Gut* 26: 1059-1064 (1985).

William L Hasler et al. "Erythromycin Contracts Rabbit Colon Myocytes via Occupation of Motilin Receptors" *The American Physiological Society* :G50-G55 (1992).

* cited by examiner

*Primary Examiner*—Bruce R. Campell
*Assistant Examiner*—Andrew D. Kosar
(74) *Attorney, Agent, or Firm*—Browdy Andneimark, PLLC

(57)  ABSTRACT

The present invention aims to provide cyclic peptide derivatives having motilin receptor antagonist activity and are useful as pharmaceuticals. The present invention provides compounds of general formula (1):

wherein $R_1$ represents an optionally substituted phenyl group or the like; $R_2$ represents an amino group or the like; $R_3$ to $R_6$ represent a hydrogen atom, a methyl group or the like; $R_7$ represents a hydrogen atom or the like; V to Z represent a carbonyl group or a methylene group; m represents an integer of 0–2; and n represents an integer of 0–3; or a hydrate or a pharmaceutically acceptable salt thereof.

21 Claims, No Drawings

CYCLIC MOTILIN RECEPTOR ANTAGONISTS

TECHNICAL FIELD

The present invention relates to cyclic peptide derivatives having motilin receptor antagonist activity or the like and useful as pharmaceuticals.

BACKGROUND ART

Among gastrointestinal hormones, motilin is a straight peptide consisting of 22 amino acids that is known to control gastrointestinal motility of mammals including human. Motilin receptors have been known to be predominantly localized in the upper gastrointestinal tract such as stomach and duodenum, and recently found to be also localized in the lower gastrointestinal tract such as large intestine (William et al., Am. J. Physiol., 262, G50–G55 (1992)), showing that motilin may be involved in the motility of not only the upper but also the lower gastrointestinal tract.

It was reported that patients of irritable bowel syndrome showing diarrhea conditions or patients of irritable bowel syndrome under stress show hypermotilinemia (Preston et al., Gut, 26, 1059–1064 (1985); Fukodo et al., Tohoku J. Exp. Med., 151, 373–385 (1987)), suggesting that increased blood motilin may be involved in this pathology. Other pathologies reported to be associated with hypermotilinemia include Crohn's disease, ulcerative colitis, pancreatitis, diabetes, obesity, malabsorption syndrome, bacterial diarrhea, atrophic gastritis, postgastrectomy/enterectomy, etc. Therefore, motilin receptor antagonists may potentially improve pathologies with increased blood motilin such as irritable bowel syndrome.

Recently, efforts have been made to develop and research motilin receptor antagonists, and various compounds have been reported (JP-A-7-138284, JP-A-2000-44595, etc.).

Especially, JP-A-7-138284 discloses cyclic peptide derivatives, which are used as pharmacological tools in studies of the effect of motilin on gastrointestinal motility or development and research of pharmaceuticals in this field of the art. However, their motilin antagonist activity is not sufficient and it would be desirable to develop cyclic peptide derivatives having higher activity.

DISCLOSURE OF THE INVENTION

An object of the present invention is to provide cyclic peptide derivatives having motilin receptor antagonist activity and useful as pharmaceuticals.

As a result of careful studies to develop novel cyclic peptide derivatives having higher motilin receptor antagonist activity, we accomplished the present invention on the basis of the finding that cyclic peptide derivatives of general formula (1) have excellent motilin receptor antagonist activity.

Accordingly, the present invention provides a compound of general formula (1):

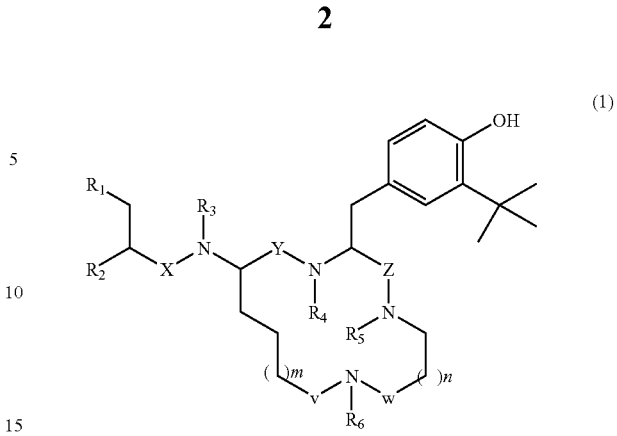

wherein
$R_1$ represents an optionally substituted phenyl group or an optionally substituted heterocycle;
$R_2$ represents a hydrogen atom or an optionally substituted amino group;
$R_3$ represents a hydrogen atom, a methyl group or an ethyl group;
$R_4$ represents a hydrogen atom, a methyl group or an ethyl group;
$R_5$ represents a hydrogen atom, a methyl group or an ethyl group;
$R_6$ represents a hydrogen atom, a methyl group, an ethyl group or —CO—$R_7$;
$R_7$ represents a hydrogen atom or a straight or branched alkyl group having 1–3 carbon atoms;
V represents a carbonyl group or a methylene group;
W represents a carbonyl group or a methylene group;
X represents a carbonyl group or a methylene group;
Y represents a carbonyl group or a methylene group;
Z represents a carbonyl group or a methylene group;
m represents a number of 0–2; and
n represents a number of 0–3;
except for the case where $R_1$ represents a phenyl group, and $R_2$ represents an amino group, and all of $R_3$, $R_4$, $R_5$ and $R_6$ represent a hydrogen atom, and V represents a methylene group, and all of W, X, Y and Z represent a carbonyl group, and both m and n represent 1; or a hydrate or a pharmaceutically acceptable salt thereof.

The present invention also provides a pharmaceutical comprising the compound of general formula (1) or a hydrate or a pharmaceutically acceptable salt thereof as an active ingredient. The present invention also provides a motilin receptor antagonist comprising the above compound or a hydrate or a pharmaceutically acceptable salt thereof. The present invention also provides a gastrointestinal motility inhibitor comprising the above compound or a hydrate or a pharmaceutically acceptable salt thereof as an active ingredient. The present invention also provides a pharmaceutical for treating hypermotilinemia comprising the above compound or a hydrate or a pharmaceutically acceptable salt thereof as an active ingredient. The above compound or a hydrate or a pharmaceutically acceptable salt thereof may also be used for preparing a pharmaceutical or a pharmaceutical composition such as motilin receptor antagonists, gastrointestinal motility depressants and pharmaceuticals for treating hypermotilinemia.

According to another aspect of the present invention, a method for treating hypermotilinemia with the above compound or a hydrate or a pharmaceutically acceptable salt thereof is provided. Preferably, a method for treating hypermotilinemia associated with irritable bowel syndrome, Crohn's disease, ulcerative colitis, pancreatitis, diabetes, obesity, malabsorption syndrome, bacterial diarrhea, atrophic gastritis, postgastrectomy/enterectomy and the like is provided. For example, a method comprising the step of administering a therapeutically effective amount of the above compound or a hydrate or a pharmaceutically acceptable salt thereof to a patient in need of such treatment is provided.

The present invention also provides a compound of general formula (2):

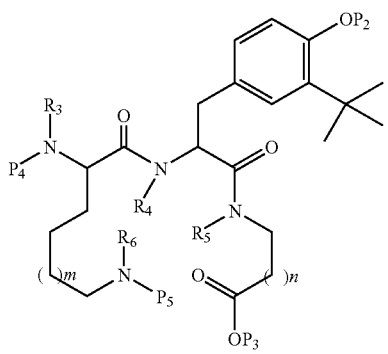

(2)

wherein $R_3$, $R_4$, $R_5$, $R_6$, m and n have the same meanings as defined for general formula (1) above;
$P_2$ represents a hydrogen atom or a protective group for a phenolic hydroxyl group;
$P_3$ represents a hydrogen atom or a protective group for a carboxyl group;
$P_4$ represents a hydrogen atom or a protective group for an amino group; and
$P_5$ represents a hydrogen atom or a protective group for an amino group; or
a hydrate or a pharmaceutically acceptable salt thereof.

The present invention also provides a compound of general formula (3):

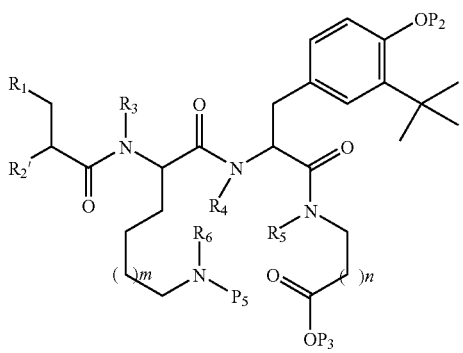

(3)

wherein $R_3$, $R_4$, $R_5$, m, n, $P_2$, $P_3$ and $P_5$ have the same meanings as defined for general formula (2) above;
$R_1$ has the same meaning as defined in general formula (1) above; and
$R_2'$ represents a hydrogen atom or an optionally substituted protected amino group; or
a hydrate or a pharmaceutically acceptable salt thereof.

The present invention also provides a compound of general formula (4):

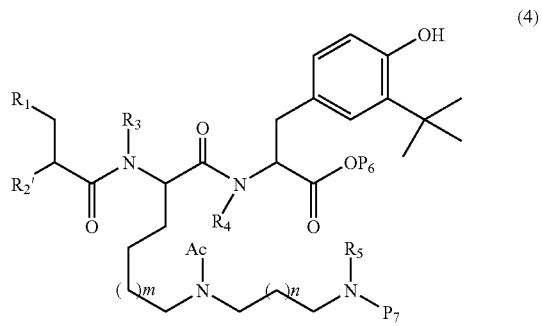

(4)

wherein $R_1$, $R_3$, $R_4$, $R_5$, $R_2'$, m and n have the same meanings as defined for general formula (3) above;
$P_6$ represents a hydrogen atom or a protective group for a carboxyl group; and
$P_7$ represents a hydrogen atom or a protective group for an amino group; or
a hydrate or a pharmaceutically acceptable salt thereof.

In the definition of the compound of general formula (1), substituents in the optionally substituted phenyl group for $R_1$ preferably include halogen atoms and trifluoromethyl, hydroxyl, amino and nitrile groups, more preferably halogen atoms, especially fluorine atom. The phenyl group may have one or more of these substituents which may be the same or different. The number of substituents is preferably 1–3, more preferably 1.

The optionally substituted phenyl group for $R_1$ may be phenyl, 4-fluorophenyl, 3-fluorophenyl, 2-fluorophenyl, 3,4-difluorophenyl, 2,3,4-trifluorophenyl, 4-chlorophenyl, 3-chlorophenyl, 2-chlorophenyl, 3,4-dichlorophenyl, 2,3,4-trichlorophenyl, 4-trifluoromethylphenyl, 3-trifluoromethylphenyl, 4-hydroxyphenyl, 3-hydroxyphenyl, 4-aminophenyl, 4-cyanophenyl, 3-cyanophenyl, 3-fluoro-4-hydroxyphenyl, 2-fluoro-4-hydroxyphenyl or the like, preferably phenyl, 4-fluorophenyl, 3-fluorophenyl, 3,4-difluorophenyl, 4-chlorophenyl, 3-chlorophenyl or 3,4-dichlorophenyl, more preferably 4-fluorophenyl.

The heterocycle in the optionally substituted heterocycle for $R_1$ may be an aliphatic or aromatic 5 to 7-membered monocycle or fused cycle containing at least one hetero atoms selected from nitrogen, sulfur and oxygen atoms, specifically pyridyl, furyl, thienyl, indolyl, quinolinyl, benzofuryl, tetrahydroisoquinolyl, preferably indolyl.

Substituents in the optionally substituted heterocycle for $R_1$ include hydroxyl, amino, carboxyl, methoxyl, methyl, ethyl, trifluoromethyl, oxo, etc., and the heterocycle may have one or more of these substituents which may be the same or different.

The optionally substituted heterocycle for $R_1$ is preferably 3-indolyl.

$R_1$ as defined above is preferably phenyl, 4-fluorophenyl, 3-fluorophenyl, 3,4-difluorophenyl, 4-chlorophenyl, 3-chlorophenyl, 3,4-dichlorophenyl or 3-indolyl, more preferably 4-fluorophenyl.

Substituents in the optionally substituted amino group for $R_2$ may be, for example, a straight or branched alkyl group having 1–3 carbon atoms, preferably methyl or ethyl. The amino group may have one or more of these substituents which may be the same or different.

The optionally substituted amino group for $R_2$ may be an amino group which may be substituted by one or more the same or different straight or branched alkyl groups having 1–3 carbon atoms, such as amino, methylamino, ethylamino, dimethylamino, among which amino is especially preferred.

$R_2$ as defined above is preferably an amino group.
$R_3$ is preferably a hydrogen atom or a methyl group.
$R_4$ is preferably a hydrogen atom or a methyl group.
$R_5$ is preferably a hydrogen atom or a methyl group.
$R_6$ is preferably a hydrogen atom, a methyl group or an acetyl group.
V is preferably a methylene group.
W is preferably a carbonyl group or a methylene group.
X is preferably a carbonyl group or a methylene group.
Y is preferably a carbonyl group.
Z is preferably a carbonyl group.
m is preferably 0 or 1.
n is preferably 0, 1 or 2.
The sum of m and n is preferably 1, 2 or 3.

In a preferred compound of general formula (1), X is a methylene group when $R_1$ a phenyl group and $R_3$ is a hydrogen atom.

In another preferred compound of general formula (1), $R_1$ is a 4-fluorophenyl group, $R_2$ is an amino group, $R_3$ is a hydrogen atom or a methyl group, $R_4$ is a hydrogen atom or a methyl group, $R_5$ is a hydrogen atom or a methyl group, $R_6$ is a hydrogen atom, a methyl group or an acetyl group, V is a methylene group, W is a carbonyl group or a methylene group, X is a carbonyl group or a methylene group, Y is a carbonyl group, Z is a carbonyl group, m is 0 or 1, n is 0, 1 or 2 and the sum of m and n is 1, 2 or 3. More preferably, the compound is any one of (2S-(2S,13S))-2-amino-N-(2-(3-tert-butyl-4-hydroxyphenylmethyl)-1,4,8-triaza-3,7,14-trioxocyclotetradec-13-yl)-3-(4-fluorophenyl)-N-methyl-propionamide, (2S-(2S,13S))-2-amino-N-(2-(3-tert-butyl-4-hydroxyphenylmethyl)-1-methyl-1,4,8-triaza-3,7,14-trioxocyclotetradec-13-yl)-3-(4-fluorophenyl)-N-methylpropionamide, (2S-(2S,12S))-2-amino-N-(2-(3-tert-butyl-4-hydroxyphenylmethyl)-1,4,8-triaza-3,7,13-trioxocyclotridec-12-yl)-3-(4-fluorophenyl)-N-methylpropionamide, (2S-(2S,13S))-2-amino-N-(2-(3-tert-butyl-4-hydroxyphenylmethyl)-4-methyl-1,4,8-triaza-3,7,14-trioxocyclotetradec-13-yl)-3-(4-fluorophenyl)-N-methylpropionamide, (2S-(2S,13S))-2-amino-N-(2-(3-tert-butyl-4-hydroxyphenylmethyl)-8-methyl-1,4,8-triaza-3,7,14-trioxocyclotetradec-13-yl)-3-(4-fluorophenyl)-N-methylpropionamide, (2S-(2S,14S))-2-amino-N-(2-(3-tert-butyl-4-hydroxyphenylmethyl)-1,4,9-triaza-3,8,15-trioxocyclopentadec-14-yl)-3-(4-fluorophenyl)-N-methylpropionamide, (2S,14S)-13-(2S-2-amino-3-(4-fluorophenyl)propylamino)-2-(3-tert-butyl-4-hydroxyphenylmethyl)-1,4,8-triaza-3,7,14-trioxocyclotetradecane, (2S-(2S,13S))-N-(8-acetyl-2-(3-tert-butyl-4-hydroxyphenylmethyl)-N-methyl-1,4,8-triaza-3,14-dioxocyclotetradec-13-yl)-2-amino-3-(4-fluorophenyl) propionamide, (2S-(2S,13S))-2-amino-N-(2-(3 -tert-butyl-4-hydroxyphenylmethyl)-9,N-dimethyl-1,4,9-triaza-3,8,14-trioxocyclotetradec-13-yl)-3-(4-fluorophenyl) propionamide, and (2S-(2S,13S))-2-amino-N-(2-(3-tert-butyl-4-hydroxyphenylmethyl)-1,4,8-triaza-3,7,14-trioxocyclotetradec-13-yl)-3-phenyl-N-methylpropionamide.

The compounds of general formulae (2)-(4) are useful as intermediates for preparing the compound of general formula (1). Protective groups for amino, carboxyl and phenolic hydroxyl groups as defined for these general formulae (2)-(4) include the following groups.

Protective groups for amino groups (i.e. $P_4$, $P_5$, $P_7$ and the protective group in $R_2'$ which is an optionally substituted protected amino group) include functional groups known to be useful as protective groups for amino groups such as benzyloxycarbonyl, t-butoxycarbonyl, 9-fluorenylmethyloxycarbonyl, allyloxycarbonyl, 2,2,2-trichloroethoxycarbonyl, benzoyl, acetyl, trifluoroacetyl, benzenesulfonyl, p-toluenesulfonyl, trimethylsilyl, t-butyldimethylsilyl, benzyl and benzyloxymethyl, preferably benzyloxycarbonyl and t-butoxycarbonyl.

Protective groups for carboxyl groups ($P_3$ and $P_6$) include functional groups known to be useful as protective groups for carboxyl groups such as methyl, ethyl, t-butyl, allyl, benzyl, 2,2,2-trichloroethyl, trimethylsilyl and t-butyldimethylsilyl, preferably methyl, benzyl and t-butyl.

Protective groups for phenolic hydroxyl groups ($P_2$) include functional groups known to be useful as protective groups for phenolic hydroxyl groups such as methyl, methoxymethyl, benzyloxymethyl, 2-methoxyethoxymethyl, 2-(trimethylsilyl)ethoxymethyl, tetrahydropyranyl, allyl, t-butyl, benzyl, 4-methoxybenzyl, 2-nitrobenzyl, trimethylsilyl, t-butyldimethylsilyl, acetyl, trifluoroacetyl, benzoyl, methoxycarbonyl, 2,2,2-trichloroethoxycarbonyl and t-butoxycarbonyl, preferably benzyl.

Acids forming a salt of the compound of formula (1), (2), (3) or (4) include inorganic acids such as hydrochloric acid, hydrobromic acid, hydroiodic acid, sulfuric acid and phosphoric acid, and organic acids such as acetic acid, oxalic acid, maleic acid, fumaric acid, citric acid, succinic acid, tartaric acid, methanesulfonic acid and trifluoroacetic acid.

Compounds of the present invention may exist as optical isomers, and such individual optical isomers and mixtures thereof are all included in the present invention.

Compounds of the present invention may also be obtained as hydrates of the compounds of formula (1), (2), (3) or (4).

The present invention is specifically explained below, in which amino acids forming peptides, protective groups and reagents are sometimes abbreviated as follows. Tyr: tyrosine; Z: benzyloxycarbonyl; Boc: tert-(or t-)butoxycarbonyl; CMPI: 2-chloro-1-methylpyridinium iodide; PyCIU: chloro-N,N,N',N'-bis(tetramethylene)formamidinium hexafluorophosphate; PyBrop: bromotripyrrolidinophosphonium hexafluorophosphate; BOP: benzotriazole-1-yloxy-tris(dimethylamino)phosphonium hexafluorophosphate; HATU: O-(7-azabenzotriazole-1-yl)-1,1,3,3-tetramethyluronium hexafluorophosphate; WSCI: N-ethyl-N'-3-dimethylaminopropyl carbodiimide; DIC: N,N'-diisopropyl carbodiimide; DCC: N,N'-dicyclohexyl carbodiimide; DPPA: diphenylphosphoryl azide; CDI: 1,1'-carbonyldiimidazole; HOBT: 1-hydroxybenzotriazole monohydrate; NMM: N-methylmorpholine; TEA: triethylamine; DIEA: diisopropylethylamine; DMAP: 4-dimethylaminopyridine; TFA: trifluoroacetic acid; THF: tetrahydrofuran; DMF: N,N-dimethylformamide; CH: chloroform; MC: methylene chloride; M: methanol; N: concentrated aqueous ammonia; EA: ethyl acetate; H: n-hexane.

PREFERRED EMBODIMENTS OF THE INVENTION

The present application claims priority based on Japanese Patent Application No. 2000-253950, the disclosure of which is incorporated herein as reference in its entirety.

Compounds of the present invention can be prepared by solid phase or liquid phase processes. In the case of solid phase processes, they can be prepared by using an automatic organic synthesizer or manually.

Compounds of the present invention can be prepared by the process of scheme 1, 2 or 3 described below, which may be modified in part as appropriate to suit the desired compound, starting from a known compound. Compounds of the present invention can also be obtained by appropriately adapting the specific processes described in the examples below.

Scheme 1

Compounds of the present invention wherein V represents a methylene group and W, X, Y and Z represent a carbonyl group can be prepared according to scheme 1 shown below using reagents having desired groups.

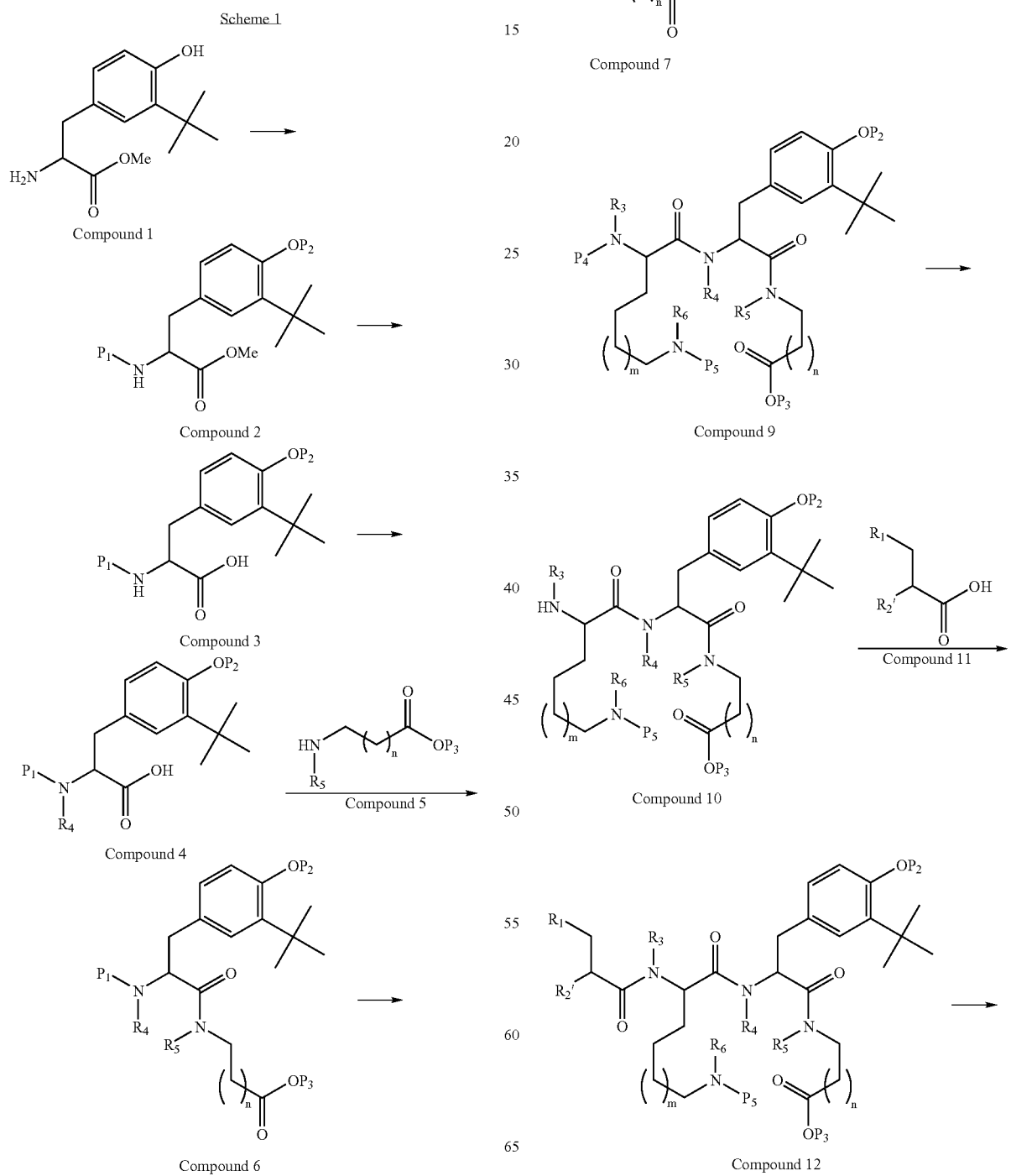

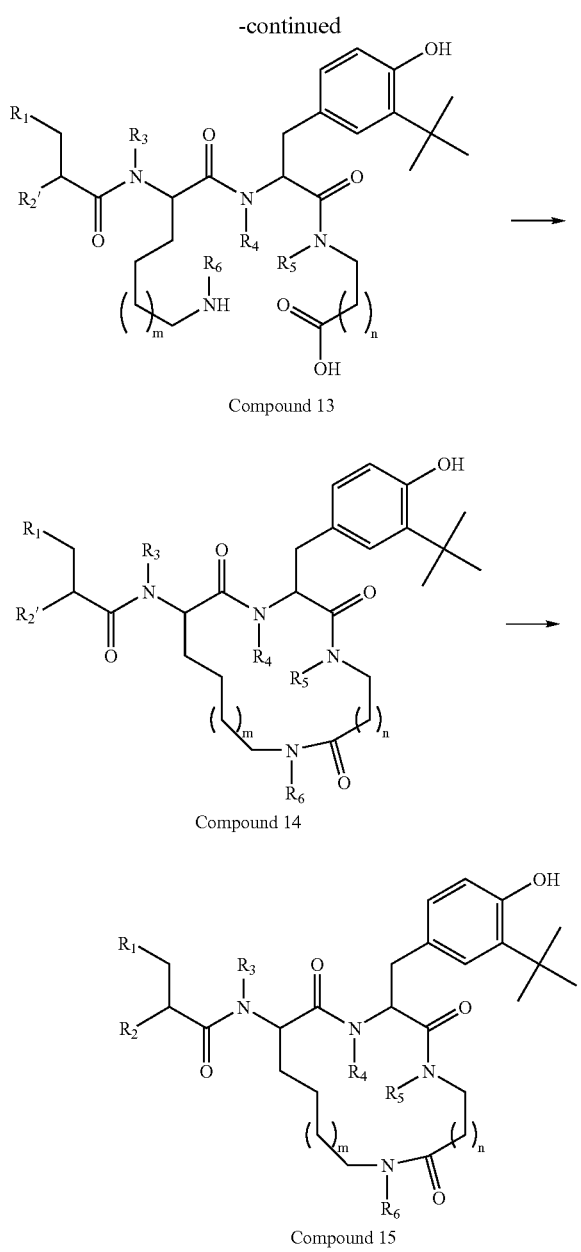

Compound 13

Compound 14

Compound 15 wherein $P_1$, $P_4$ and $P_5$ represent a protective group for an amino group, $P_2$ represents a hydrogen atom or a protective group for a phenolic hydroxyl group, $P_3$ represents a protective group for a carboxyl group, $R_2'$ represents a hydrogen atom or an optionally substituted protected amino group and the other symbols have the same meanings as defined in claim 1.

In scheme 1, conversion from compound 1 (described in Example 1(1) of JPA 2000-44595) into compound 2 can be performed by protecting the amino group of compound 1 and then, if desired, protecting the phenol group. Specifically, compound 2 wherein $P_2$ is a hydrogen atom can be obtained by reacting compound 1 with a protective group-introducing reagent such as benzyloxycarbonyl chloride or di-t-butyl dicarbonate in a mixed solvent of dioxane and water in the presence of a base such as sodium carbonate with ice cooling or at room temperature. Compound 2 wherein $P_2$ is a protective group (especially, benzyl) can be obtained by further reacting the compound with benzyl chloride or the like in DMF or THF in the presence of a base such as sodium hydride with ice cooling.

Conversion from compound 2 into compound 3 can be performed by treating the methyl ester group of compound 2 with a base to hydrolyze it. Specifically, compound 3 can be obtained by stirring compound 2 with a base such as sodium hydroxide or lithium hydroxide in a mixed solvent of methanol and water or dioxane and water with ice cooling or at room temperature.

Conversion from compound 3 into compound 4 can be performed by reacting compound 3 with a methylating agent or an ethylating agent in the presence of a base. Specifically, compound 4 can be obtained by reacting compound 3 with methyl iodide, dimethyl sulfate or ethyl iodide or the like in DMF or THF or a mixed solvent of DMF and THF in the presence of a base such as sodium hydride with ice cooling. The phenolic hydroxyl group here is preferably protected by $P_2$. This methylation or ethylation reaction is unnecessary for compounds wherein $R_4$ is a hydrogen atom.

Conversion from compound 4 into compound 6 is performed by reacting compound 4 with compound 5. This reaction can be performed by condensing the carboxyl group of compound 4 with the amino group of compound 5 using a known conventional condensing reagent. Specifically, compound 6 can be obtained by stirring a mixture of compound 4, compound 5 and one of condensing agents such as CMPI, BOP, PyCIU, PyBrop, HATU, DCC, DIC, WSCI, DPPA and CDI in a reaction solvent such as THF or DMF or methylene chloride. The reaction here is often preferably promoted by adding a base such as TEA, DIEA, NMM, pyridine and DMAP or adding an additive such as HOBT as appropriate. Compound 5 may be commercially available. If not commercially available, compound 5 wherein $R_5$ is a hydrogen atom can be prepared by esterifying a suitable α-, β-, γ- or δ-amino acid. Compound 5 wherein $R_5$ is a methyl or ethyl group can be obtained by protecting the amino group of a suitable α-, β-, γ- or δ-amino acid ester with a benzyloxycarbonyl group or a t-butoxycarbonyl group in the same manner as described for the conversion from compound 1 into compound 2, methylating or ethylating the amino acid ester in the same manner as described for the conversion from compound 3 into compound 4, and then eliminating the amino-protecting group by a conventional method.

Conversion from compound 6 into compound 7 can be performed by eliminating the amino-protecting group $P_1$ of compound 6. A specific deprotecting method comprises hydrogenolysis using a palladium catalyst when $P_1$ is a benzyloxycarbonyl group or treatment with an acid such as TFA when it is a t-butoxycarbonyl group.

Conversion from compound 7 into compound 9 is performed by reacting compound 7 with compound 8. This reaction can be performed by condensing the amino group of compound 7 with the carboxyl group of compound 8 using a known conventional condensing reagent. Specifically, compound 9 can be obtained by the same procedure as described for the conversion from compound 4 into compound 6. Compound 8 may be commercially available. If not commercially available, it can be obtained by simultaneously methylating both protected amino groups of a precursor of compound 8 wherein the α-amino group and the pendant amino group corresponding to $R_3$ and $R_6$ are protected by $P_4$ and $P_5$ respectively ($P_4$ and $P_5$ are preferably different protective groups) in the same manner as described for the conversion from compound 3 into compound 4. Compounds 8 other than those wherein both $R_3$ and $R_6$ represent a methyl group can also be prepared by appropriately adapting this procedure.

Conversion from compound 9 into compound 10 can be performed by eliminating the amino-protecting group $P_4$ of compound 9. A specific deprotecting method comprises hydrogenolysis using a palladium catalyst when $P_4$ is a benzyloxycarbonyl group or treatment with an acid such as TFA when it is a t-butoxycarbonyl group.

Conversion from compound 10 into compound 12 is performed by reacting compound 10 with compound 11. This reaction can be performed by condensing the amino group of compound 10 with the carboxyl group of compound 11 using a known conventional condensing reagent. Specifically, compound 12 can be obtained by the same procedure as described for the conversion from compound 4 into compound 6. Compound 11 may be commercially available. If not commercially available, compound 11 wherein $R_2'$ is a protected methylamino group can be obtained by methylating a precursor of compound 11 wherein the group corresponding to $R_2'$ is a protected amino group in the same manner as described for the conversion from compound 3 into compound 4. Compounds 11 other than those wherein the group corresponding to $R_2'$ is a protected amino group can also be prepared by appropriately adapting this procedure.

Conversion from compound 12 into compound 13 can be performed by simultaneously or stepwise eliminating the amino-protecting group $P_5$, carboxyl-protecting group $P_3$ and phenol-protecting group $P_2$ of compound 12. A specific deprotecting method comprises hydrogenolysis using a palladium catalyst when $P_5$ is a benzyloxycarbonyl group, $P_3$ is a benzyl group and $P_2$ is a benzyl group or treatment with an acid such as TFA when $P_5$ is a t-butoxycarbonyl group and $P_3$ is t-butyl or alkali hydrolysis when $P_3$ is a methyl group, for example.

Conversion from compound 13 into compound 14 can be performed by intramolecular cyclization of the amino group and the carboxyl group of compound 13 using a condensing reagent known to be useful for macrocycle formation reaction. Specifically, compound 14 can be obtained by stirring compound 13 at room temperature under dilute conditions (at a concentration of compound 13 of about 0.005–0.02 M, preferably 0.01 M) using DMF, BOP and pyridine as reaction solvent, condensing agent and base, respectively.

When $R_2'$ of compound 14 is an optionally substituted protected amino group, conversion from compound 14 into compound 15 can be performed by deprotecting the amino group. A specific method comprises hydrogenolysis using a palladium catalyst when the amino-protecting group of $R_2'$ is a benzyloxycarbonyl group or treatment with an acid such as TFA when it is a t-butoxycarbonyl group. When $R_2'$ is a hydrogen atom, compound 14 is a desired compound.

Scheme 2

Compounds of the present invention wherein V and X represent a methylene group and W, Y and Z represent a carbonyl group can be prepared according to scheme 2 shown below using reagents having desired groups.

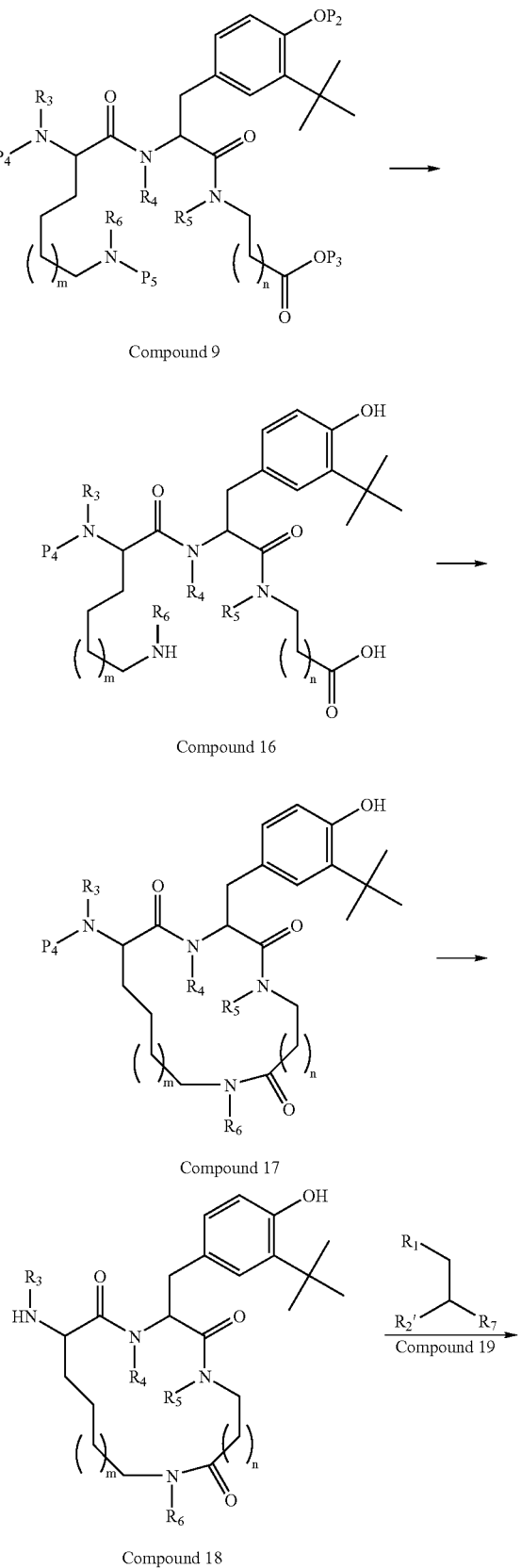

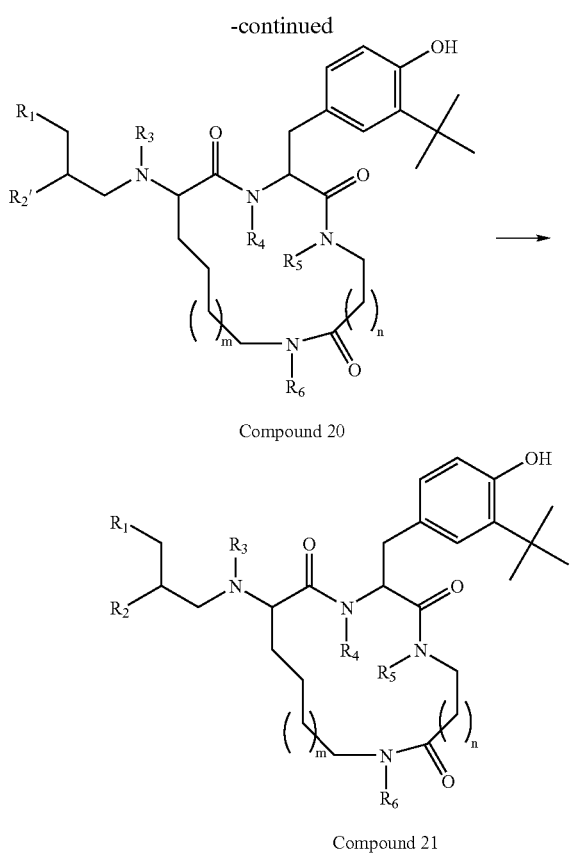

Compound 20

Compound 21 wherein $P_4$ and $P_5$ represent a protective group for an amino group, $P_2$ represents a hydrogen atom or a protective group for a phenolic hydroxyl group, $P_3$ represents a protective group for a carboxyl group, $R_2'$ represents a hydrogen atom or an optionally substituted protected amino group when $R_2$ of the desired compound represents an optionally substituted amino group, $R_7$ represents a functional group capable of reacting with an amino group to form a bond such as formyl, —$CH_2Hal$ where Hal represents a halogen atom such as a chlorine, bromine or iodine atom, —$CH_2OSO_2R$ where R represents a methyl, trifluoromethyl, tosyl or the like group, and the other symbols have the same meanings as defined in claim 1.

Conversion from compound 9 into compound 16 can be performed by simultaneously or stepwise eliminating the amino-protecting group $P_5$, carboxyl-protecting group $P_3$ and phenol-protecting group $P_2$ of compound 9. A specific deprotecting method comprises hydrogenolysis using a palladium catalyst when $P_5$ is a benzyloxycarbonyl group, $P_3$ is a benzyl group and $P_2$ is a benzyl group or treatment with an acid such as TFA when $P_5$ is a t-butoxycarbonyl group and $P_3$ is t-butyl or alkali hydrolysis when $P_3$ is a methyl group, for example.

Conversion from compound 16 into compound 17 can be performed by intramolecular cyclization of the amino group and the carboxyl group of compound 16 using a condensing reagent known to be useful for macrocycle formation reaction. Specifically, compound 17 can be obtained by stirring compound 16 at room temperature under dilute conditions (at a concentration of compound 16 of about 0.005–0.02 M, preferably 0.01 M) using DMF, BOP and pyridine as reaction solvent, condensing agent and base, respectively.

Conversion from compound 17 into compound 18 can be performed by eliminating the amino-protecting group $P_4$ of compound 17. A specific deprotecting method comprises hydrogenolysis using a palladium catalyst when $P_4$ is a benzyloxycarbonyl group or treatment with an acid such as TFA when it is a t-butoxycarbonyl group.

Conversion from compound 18 into compound 20 is performed by reacting compound 18 with compound 19. When $R_7$ of compound 19 is a formyl group, this reaction can be performed by reductively forming a bond between this formyl group and the amino group of compound 18, specifically stirring a mixture of compound 18 and compound 19 with sodium cyanoborohydride and acetic acid in a reaction solvent such as methanol or acetonitrile, for example. When $R_7$ of compound 19 is —$CH_2Hal$ or —$CH_2OSO_2R$ or the like, the reaction can be performed by alkylating the amino group of compound 18. Compound 19 here wherein $R_7$ is a formyl group and $R_2'$ is an optionally substituted protected amino group, for example, can be obtained by condensing the carboxyl group of compound 11 used in scheme 1 wherein $R_2'$ represents an optionally substituted protected amino group with N,O-dimethylhydroxylamine to convert it into an N-methoxy-N-methylcarbamoyl group and then reducing the N-methoxy-N-methylcarbamoyl group with lithium aluminium hydride, for example.

When $R_2'$ of compound 20 is an optionally substituted protected amino group, conversion from compound 20 into compound 21 can be performed by deprotecting the amino group, specifically catalytic hydrogenation when the amino-protecting group of $R_2'$ is a benzyloxycarbonyl group or treatment with an acid such as TFA when it is a t-butoxycarbonyl group. When $R_2'$ is a hydrogen atom, compound 21 is a desired compound.

Scheme 3

Compounds of the present invention wherein $R_6$ represents an acetyl group, V and W represent a methylene group and X, Y and Z represent a carbonyl group can be prepared according to scheme 3 shown below using reagents having desired groups.

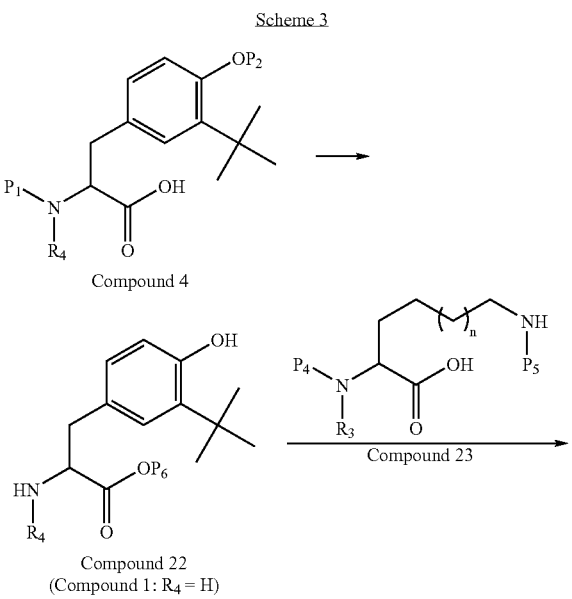

Scheme 3

Compound 4

Compound 22
(Compound 1: $R_4$ = H)

Compound 23

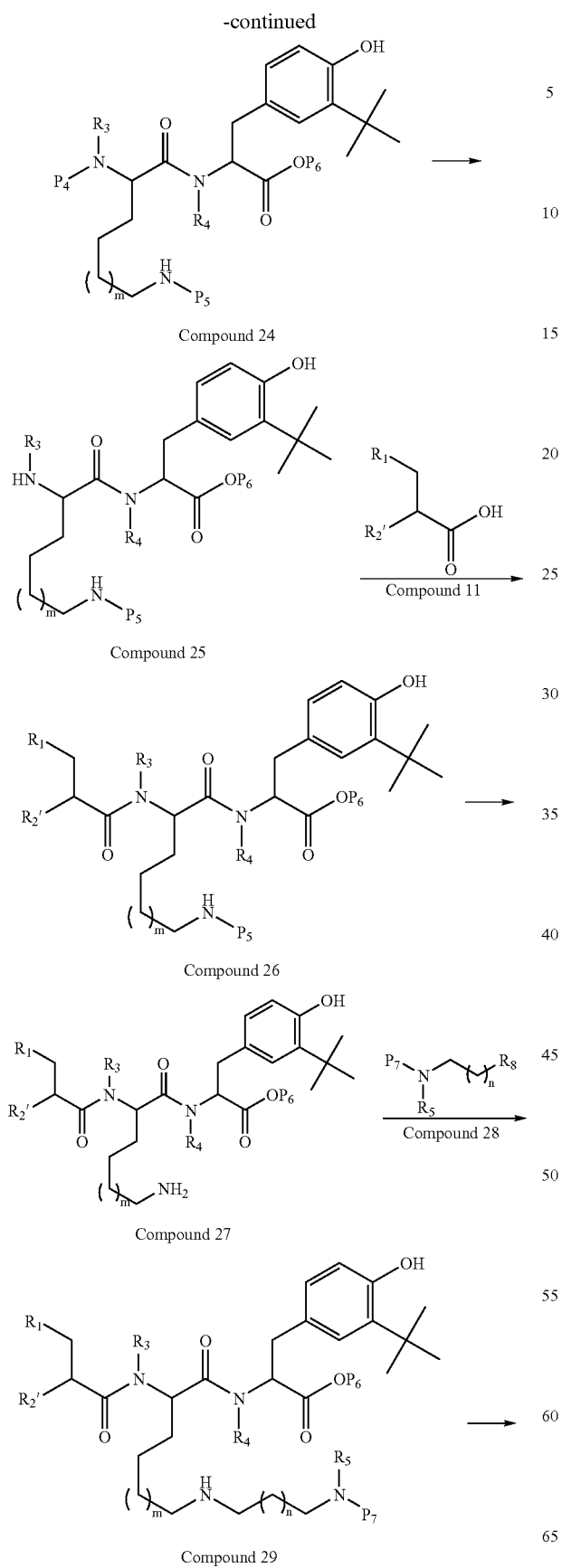
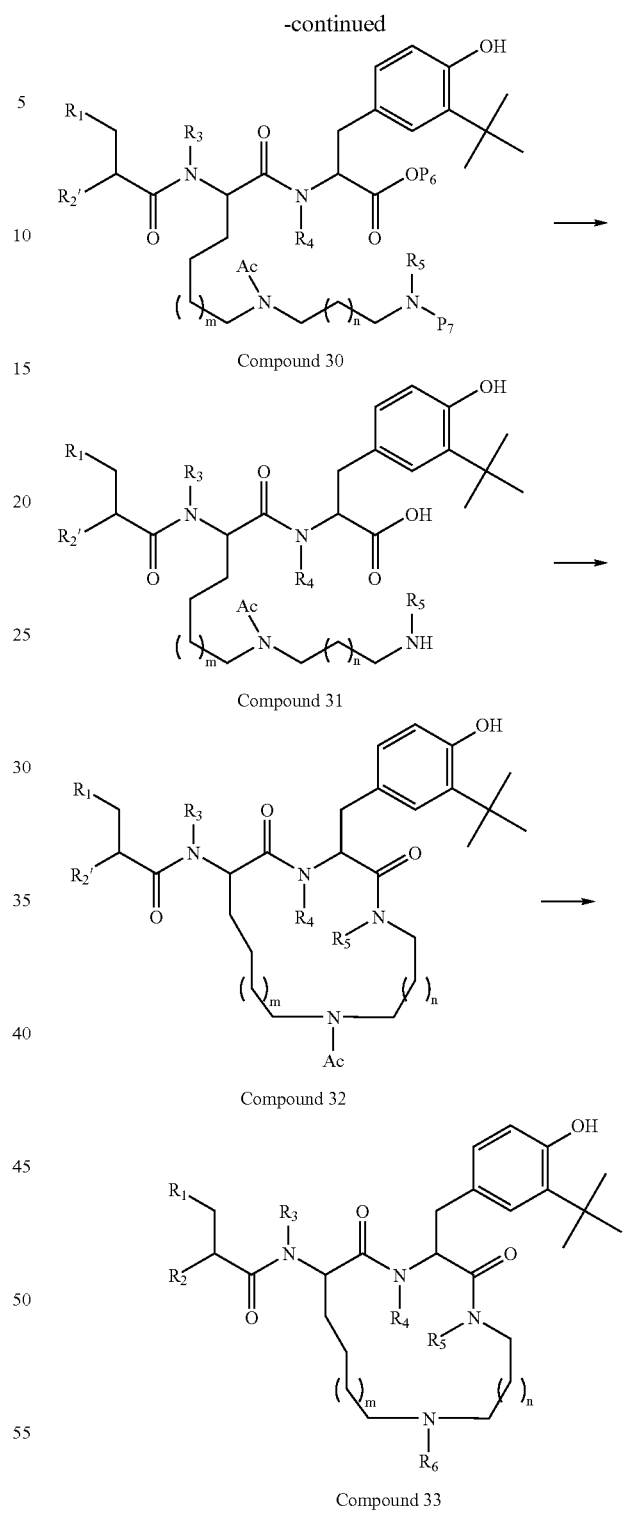

wherein $P_1$, $P_4$, $P_5$ and $P_7$ represent a protective group for an amino group, $P_2$ represents a hydrogen atom or a protective group for a phenolic hydroxyl group, $P_6$ represents a protective group for a carboxyl group, $R_2'$ represents a hydrogen atom or an optionally substituted protected amino group when $R_2$ of the desired compound represents an optionally substituted amino group, $R_8$ represents a functional group capable of reacting with an amino group to form a bond such as formyl, —CH$_2$Hal where Hal represents a halogen atom such as a chlorine, bromine or iodine atom, —CH$_2$OSO$_2$R where R represents a methyl, trifluoromethyl, tosyl or the like group, and the other symbols have the same meanings as defined in claim 1.

Conversion from compound 4 into compound 22 can be performed by successively esterifying the carboxyl group of compound 4 with P$_6$ and eliminating the amino-protecting group P$_1$ and phenol-protecting group P$_2$. Specifically, the carboxyl group can be esterified with P$_6$ into a benzyl ester by condensation reaction with benzyl alcohol or into a t-butyl ester by a reaction with isobutene and an acid or into a methyl ester by a reaction with methanol or methylation reaction with diazomethane. The amino-protecting group can be eliminated by treatment with an acid such as TFA when it is a t-butoxycarboxy group or hydrogenolysis using a palladium catalyst when it is a benzyloxycarboxy group. When the phenol-protecting group P$_2$ is a t-butyl or benzyl group, P$_1$ and P$_2$ can be simultaneously eliminated. Compound 22 wherein R$_4$ is a hydrogen atom and P$_6$ is a methyl group is compound 1.

Conversion from compound 22 (or compound 1) into compound 24 is performed by reacting compound 22 (or compound 1) with compound 23. This reaction can be performed by condensing the amino group of compound 22 (or compound 1) with the carboxyl group of compound 23 using a known conventional condensing reagent. Specifically, compound 24 can be obtained by the same procedure as described for the conversion from compound 4 into compound 6 in scheme 1. Compound 23 may be commercially available. If not commercially available, it can be obtained by adapting the process for compound 8 described in scheme 1. Compound 23 wherein m is 1, R$_3$ is a hydrogen atom or a methyl group, any one of P$_4$ and P$_5$ is a t-butoxycarbonyl group and the other is a benzyloxycarbonyl group is commercially available.

Conversion from compound 24 into compound 25 can be performed by eliminating the amino-protecting group P$_4$ of compound 24. A specific deprotecting method comprises hydrogenolysis using a palladium catalyst when P$_4$ is a benzyloxycarbonyl group or treatment with an acid such as TFA when it is a t-butoxycarbonyl group.

Conversion from compound 25 into compound 26 is performed by reacting compound 25 with compound 11 used in scheme 1. This reaction can be performed by condensing the amino group of compound 25 with the carboxyl group of compound 11 used in scheme 1 using a known conventional condensing reagent. Specifically, compound 26 can be obtained by the same procedure as described for the conversion from compound 4 into compound 6 in scheme 1.

Conversion from compound 26 into compound 27 can be performed by eliminating the amino-protecting group P$_5$ of compound 26. A specific deprotecting method comprises hydrogenolysis using a palladium catalyst when P$_5$ is a benzyloxycarbonyl group or treatment with an acid such as TFA when it is a t-butoxycarbonyl group.

Conversion from compound 27 into compound 29 is performed by reacting compound 27 with compound 28. When R$_8$ of compound 28 is a formyl group, this reaction can be performed by reductively forming a bond with the amino group of compound 27, specifically stirring a mixture of compound 27 and compound 28 with sodium cyanoborohydride and acetic acid in a reaction solvent such as methanol or acetonitrile, for example. When R$_7$ of compound 28 is —CH$_2$Hal or —CH$_2$OSO$_2$R or the like, the reaction can be performed by alkylating the amino group of compound 27. Compound 28 here wherein R$_8$ is a formyl group, for example, can be obtained by reducing the carboxyl group of a precursor of compound 28 wherein the group corresponding to R$_8$ is a carboxyl group with borane or the like into a hydroxymethyl group and then oxidizing the hydroxymethyl group into a formyl group by the Swern method or the like, for example. Alternatively, it can also be obtained by condensing the carboxyl group of a precursor of compound 28 wherein the group corresponding to R$_8$ is a carboxyl group with N,O-dimethylhydroxylamine to convert it into an N-methoxy-N-methylcarbamoyl group and then reducing the N-methoxy-N-methylcarbamoyl group with lithium aluminium hydride.

Conversion from compound 29 into compound 30 can be performed by acetylating the secondary amino group of compound 29. Specifically, compound 29 can be reacted with an acetylating agent such as acetyl chloride or acetic anhydride in a reaction solvent such as methylene chloride, THF or ethyl acetate in the presence of a base such as TEA, DIEA, pyridine or DMAP, for example.

Conversion from compound 30 into compound 31 can be performed by simultaneously or stepwise eliminating the amino-protecting group P$_7$ and the carboxyl-protecting group P$_6$ of compound 30. A specific deprotecting method comprises hydrogenolysis using a palladium catalyst when P$_7$ is a benzyloxycarbonyl group and P$_6$ is a benzyl group or treatment with an acid such as TFA when P$_7$ is a t-butoxycarbonyl group and P$_6$ is t-butyl or alkali hydrolysis when P$_6$ is a methyl group.

Conversion from compound 31 into compound 32 can be performed by intramolecular cyclization of the amino group and the carboxyl group of compound 31 using a condensing reagent known to be useful for macrocycle formation reaction. Specifically, compound 32 can be obtained by, for example, stirring compound 31 at room temperature under dilute conditions (at a concentration of compound 31 of about 0.005–0.02 M, preferably 0.01 M) using DMF, BOP and pyridine as reaction solvent, condensing agent and base, respectively.

When R$_2$' of compound 32 is an optionally substituted protected amino group, conversion from compound 32 into compound 33 can be performed by deprotecting the amino group, specifically hydrogenolysis using a palladium catalyst when the amino-protecting group of R$_2$' is a benzyloxycarbonyl group or treatment with an acid such as TFA when it is a t-butoxycarbonyl group. When R$_2$' is a hydrogen atom, compound 32 is a desired compound.

Alternatively, compounds of the present invention can be prepared by appropriately adapting the specific processes described in the examples below.

EXAMPLES

The following examples further illustrate the present invention without, however, limiting the invention thereto. The chemical structural formulae of the compounds of the examples are shown in Table A-1 and Table A-2 below.

TABLE A-1

| Example No. | Structural formula |
|---|---|
| 1 | |
| 2 | |
| 3 | |
| 4 | |

TABLE A-1-continued

| Example No. | Structural formula |
|---|---|
| 5 | (structure) |
| 6 | (structure) |
| 7 | (structure) |
| 8 | (structure) |

TABLE A-1-continued

| Example No. | Structural formula |
|---|---|
| 9 | (structure) |
| 10 | (structure) |

In the following examples, ¹H-NMR and mass spectra were measured with the following instruments. ¹H-NMR: JEOL JNM-EX-270 (270 MHz)
Mass spectra (FAB-MS): JASCO 70-250SEQ

Example 1

Synthesis of (2S-(2S,13S))-2-amino-N-(2-(3-tert-butyl-4-hydroxyphenylmethyl)-1,4,8-triaza-3,7,14-trioxocyclotetradec-13-yl)-3-(4-fluorophenyl)-N-methylpropionamide (1) Synthesis of Boc-Tyr(3-tert-Bu)-OH To a mixed solution of 14.7 g (58.5 mmol) of H-Tyr(3-tert-Bu)-OMe and 9.30 g (87.8 mmol) of sodium carbonate in 100 ml of 1,4-dioxane and 100 ml of water was added 13.4 g (61.4 mmol) of di(tert-butyl) dicarbonate with ice cooling and the mixture was stirred at room temperature for 1 hour. The reaction solution was combined with water and extracted with ethyl acetate, and then the extract was successively washed with saturated aqueous NaHCO₃ solution and saturated aqueous sodium chloride solution. The organic layer was dried over anhydrous magnesium sulfate, and then the solvent was distilled off under reduced pressure to give 24.2 g of crude Boc-Tyr (3-tert-Bu)-OMe.

To a mixed solution of 16.5 g of the crude Boc-Tyr (3-tert-Bu)-OMe in 120 ml of methanol and 40 ml of water was added 3.30 g (78.8 mmol) of lithium hydroxide monohydrate and the mixture was stirred at room temperature for 80 minutes. The reaction solution was neutralized with 2N hydrochloric acid with ice cooling and then acidified with 10% aqueous citric acid. The reaction solution was extracted with methylene chloride and dried over anhydrous magnesium sulfate, and then concentrated under reduced pressure to give 15.0 g (quant.) of the title compound.

(2) Synthesis of Boc-Tyr (3-tert-Bu)-β-Ala-OBzl

To a solution of 2.50 g (7.42 mmol) of Boc-Tyr (3-tert-Bu)-OH and 2.87 g (8.16 mmol) of H-β-Ala-OBzl p-toluenesulfonate in 22 ml of DMF were added 1.00 g (7.42 mmol) of HOBt, 0.848 ml (7.42 mmol) of NMM and 1.56 g (8.16 mmol) of WSCI with ice cooling, and the mixture was stirred at room temperature for 150 minutes. The reaction solution was combined with water and extracted with ethyl acetate, and then the extract was successively washed with saturated aqueous NH₄Cl solution, saturated aqueous NaHCO₃ solution and saturated aqueous sodium chloride solution. The organic layer was dried over magnesium sulfate, and then the solvent was distilled off under reduced pressure to give 3.57 g (97%) of Boc-Tyr (3-tert-Bu)-β-Ala-OBzl.

¹H-NMR (CDCl₃): δ 1.38 (9H, s), 1.41 (9H, s), 2.40–2.58 (2H, m), 2.84–3.00 (2H, m), 3.38–3.50 (2H, m), 4.14–4.26 (1H, m), 5.00 (1H, brs), 5.09 (2H, s), 6.20–6.30 (1H, m), 6.54 (1H, d, J=8.2 Hz), 6.85 (1H, dd, J=1.7, 8.2 Hz), 7.03 (1H, d, J=1.7 Hz), 7.30–7.40 (5H, m).

(3) Synthesis of H-Tyr (3-tert-Bu)-β-Ala-OBzl

To a solution of 3.55 g (7.13 mmol) of Boc-Tyr (3-tert-Bu)-β-Ala-OBzl in 30 ml of methylene chloride was added 20 ml of TFA and the mixture was stirred at room temperature for 40 minutes. The reaction solution was distilled off under reduced pressure, and the residue was neutralized with saturated aqueous NaHCO₃ solution, extracted with chloroform and the extract was washed with saturated aqueous sodium chloride solution. The organic layer was dried over magnesium sulfate, and then the solvent was distilled off under reduced pressured to give 2.60 g (92%) of H-Tyr (3-tert-Bu)-β-Ala-OBzl.

¹H-NMR (CDCl₃): δ 1.39 (9H, s), 2.58 (2H, t, J=6.3 Hz), 2.92 (1H, d, J=9.5 Hz), 3.13 (1H, dd, J=4.0, 13.9 Hz), 3.48–3.60 (3H, m), 5.14 (2H, s), 6.60 (1H, d, J=8.2 Hz), 6.88 (1H, dd, J=2.0, 8.2 Hz), 7.07 (1H, d, J=2.0 Hz), 7.30–7.40 (5H, m), 7.58–7.66 (1H, m).

(4) Synthesis of Boc-N-Me-Lys (Z)-Tyr (3-tert-Bu)-β-Ala-OBzl

To a solution of 2.10 g (5.28 mmol) of H-Tyr (3-tert-Bu)-β-Ala-OBzl and 3.19 g (5.54 mmol) of Boc-N-Me-Lys (Z)-OH dicyclohexylammonium salt in 22 ml of DMF were added 713 mg (5.28 mmol) of HOBt, 0.60 ml (5.25 mmol) of NMM and 1.06 g (5.54 mmol) of WSCI with ice cooling, and the mixture was stirred at room temperature for 2 hours. The reaction solution was combined with water and extracted with ethyl acetate, and then the extract was successively washed with 10% aqueous citric acid solution, saturated aqueous NaHCO₃ solution and saturated aqueous sodium chloride solution. The organic layer was dried over magnesium sulfate, and then the solvent was distilled off under reduced pressure to give 3.42 g (84%) of Boc-N-Me-Lys (Z)-Tyr (3-tert-Bu)-β-Ala-OBzl.

¹H-NMR (CDCl₃): δ 1.14–1.60 (5H, m), 1.37 (9H, s), 1.45 (9H, s), 1.72–1.90 (1H, m), 2.40–2.54 (2H, m), 2.55 (3H, s), 2.86–3.02 (2H, m), 3.06–3.22 (2H, m), 3.36–3.50 (2H, m), 4.34–4.56 (2H, m), 4.76–4.88 (1H, m), 5.09 (4H, s), 5.31 (1H, s), 6.30–6.60 (2H, m), 6.58 (1H, d, J=8.2 Hz), 6.83 (1H, dd, J=1.9, 8.2 Hz), 7.04 (1H, d, J=1.9 Hz), 7.30–7.42 (10H, m).

(5) Synthesis of N-Me-Lys (Z)-Tyr (3-tert-Bu)-β-Ala-OBzl

To a solution of 3.10 g (4.01 mmol) of Boc-N-Me-Lys (Z)-Tyr (3-tert-Bu)-β-Ala-OBzl in 20 ml of methylene chloride was added 10 ml of TFA and the mixture was stirred at room temperature for 90 minutes. The reaction solution was distilled off under reduced pressure, and the residue was neutralized with saturated aqueous NaHCO₃ solution, extracted with chloroform and the extract was washed with saturated aqueous sodium chloride solution. The organic layer was dried over magnesium sulfate, and then the solvent was distilled off under reduced pressure to give 2.59 g (96%) of N-Me-Lys (Z)-Tyr (3-tert-Bu)-β-Ala-OBzl.

¹H-NMR (CDCl₃): δ 0.80–1.40 (6H, m), 1.38 (9H, s), 2.30 (3H, s), 2.56 (2H, t, J=6.3 Hz), 2.70–3.24 (5H, m), 3.53 (2H, q, J=6.3 Hz), 4.48–4.60 (1H, m), 4.80–4.90 (1H, m), 5.12 (2H, s), 5.15 (2H, s), 6.62–6.86 (3H, m), 7.04 (1H, d, J=1.3 Hz), 7.30–7.42 (10H, m).

(6) Synthesis of Boc-Phe (4-F)-N-Me-Lys (Z)-Tyr (3-tert-Bu)-β-Ala-OBzl

To a solution of 2.50 g (3.71 mmol) of N-Me-Lys (Z)-Tyr (3-tert-Bu)-β-Ala-OBzl and 1.26 g (4.48 mmol) of Boc-Phe (4-F)-OH in 18.5 ml of THF were added 1.14 g (4.45 mmol) of CMPI and 1.29 ml (9.28 mmol) of TEA with ice cooling and the mixture was stirred at room temperature for 3 hours. The reaction solution was combined with water and extracted with ethyl acetate, and then the extract was washed with saturated aqueous sodium chloride solution. The organic layer was dried over magnesium sulfate, and then the solvent was distilled off under reduced pressure, and the residue was purified by silica gel column chromatography (developing solvent; ethyl acetate:hexane=1:1) to give 3.48 g (100%) of Boc-Phe (4-F)-N-Me-Lys (Z)-Tyr (3-tert-Bu)-β-Ala-OBzl.

¹H-NMR (CDCl₃): δ 0.80–1.40 (6H, m), 1.33, 1.36 and 1.39 (total 18H, s), 2.17 and 2.61 (total 3H, s), 2.44–3.60 (10H, m), 4.30–4.94 (3H, m), 5.01, 5.04 and 5.10 (total 4H, s), 5.20–5.48 (1H, m), 6.28–7.20 (10H, m), 7.30–7.42 (10H, m).

(7) Synthesis of (2S-(2S,13S))-2-tert-butoxycarbonylamino-N-(2-(3-tert-butyl-4-hydroxyphenylmethyl)-1,4,8-triaza-3,7,14-trioxocyclotetradec-13-yl)-3-(4-fluorophenyl)-N-methylpropionamide To a solution of 2.72 g (2.90 mmol) of Boc-Phe (4-F)-N-Me-Lys (Z)-Tyr (3-tert-Bu)-β-Ala-OBzl in 50 ml of methanol was added 270 mg of 10% palladium on carbon, and the mixture was stirred overnight at room temperature under a hydrogen atmosphere. After filtration, the filtrate was concentrated under reduced pressure to give 2.02 g (97%) of Boc-Phe (4-F)-N-Me-Lys-Tyr (3-tert-Bu)-β-Ala-OH.

To a mixed solution of 2.02 g (2.83 mmol) of the Boc-Phe (4-F)-N-Me-Lys-Tyr (3-tert-Bu)-β-Ala-OH in 140 ml of DMF and 140 ml of pyridine was added 3.13 g (7.08 mmol) of BOP reagent and the mixture was stirred at room temperature for 18 hours. The reaction solution was combined with water and extracted with ethyl acetate, and the extract was successively washed with saturated aqueous NH₄Cl solution, saturated aqueous NaHCO₃ solution and saturated aqueous sodium chloride solution. The organic layer was dried over magnesium sulfate, and then the solvent was distilled off under reduced pressure, and the residue was purified by silica gel column chromatography (developing solvent; chloroform:methanol=20:1) to give 1.37 g (69%) of (2S-(2S,13S))-2-tert-butoxycarbonylamino-N-(2-(3-tert-butyl-4-hydroxyphenylmethyl)-1,4,8-triaza-3,7,14-trioxocyclotetradec-13-yl)-3-(4-fluorophenyl)-N-methylpropionamide.

¹H-NMR (CDCl₃): δ 1.00–2.02 (6H, m), 1.33, 1.37 and 1.39 (total 18H, s), 2.30 (3H, s), 2.24–3.86 (10H, m), 4.40–4.90 (4H, m), 5.38–5.60 (2H, m), 6.00–6.20 (1H, m), 6.60–7.18 (7H, m), 6.54–7.22 (7H, m).

(8) Synthesis of (2S-(2S,13S))-2-amino-N-(2-(3-tert-butyl-4-hydroxyphenylmethyl)-1,4,8-triaza-3,7,14-trioxocyclotetradec-13-yl)-3-(4-fluorophenyl)-N-methylpropionamide To a solution of 1.25 g (1.79 mmol) of (2S-(2S,13S))-2-tert-butoxycarbonylamino-N-(2-(3-tert-butyl-4-hydroxyphenylmethyl)-1,4,8-triaza-3,7,14-trioxocyclotetradec-13-yl)-3-(4-fluorophenyl)-N-methylpropionamide in 20 ml of methylene chloride was added 10 ml of TFA and the mixture was stirred at room temperature for 40 minutes. The reaction solution was distilled off under reduced pressure, and the residue was neutralized with saturated aqueous NaHCO₃ solution, extracted with chloroform and the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol=20:1) to give 657 mg (61%) of the title compound.

FAB-MS (M$^+$+1): 598. $^1$H-NMR (DMSO-d): δ 0.60–1.92 (6H, m), 1.27 and 1.28 (total 9H, s), 2.06–2.26 (2H, m), 2.54–2.90 (4H, m), 2.65 (3H, s), 3.06–3.60 (4H, m), 3.62–4.94 (3H, m), 6.54–7.22 (7H, m), 7.50–8.50 (3H, m), 9.01 and 9.10 (total 1H, s).

Example 2

Synthesis of (2S-(2S.13S))-2-amino-N-(2-(3-tert-butyl-4-hydroxyphenylmethyl)-1-methyl-1,4,8-triaza-3,7,14-trioxocyclotetradec-13-yl)-3-(4-fluorophenyl)-N-methylpropionamide (1) Synthesis of Boc-Phe (4-benzyloxy-3-tert-Bu)-OMe A suspension of 7.5 g of the crude Boc-Tyr (3-tert-Bu)-OMe obtained in Example 1 (1) and 8.85 g.(64.0 mmol) of potassium carbonate in 45 ml of DMF was stirred at room temperature for 2.5 hours, and then 4.6 ml (38.3 mmol) of benzyl bromide was added. The mixture was stirred overnight and then combined with water and extracted with ethyl acetate. The organic layer was washed with saturated aqueous sodium chloride solution and dried over anhydrous magnesium sulfate and then concentrated under reduced pressure, and the residue was purified by silica gel column chromatography (developing solvent; ethyl acetate:n-hexane=1:5) to give 7.5 g (94%) of the title compound.

(2) Synthesis of Boc-N-Me-Phe (4-benzyloxy-3-tert-Bu)-OH

To a mixed solution of 7.5 g (17.0 mmol) of Boc-Phe (4-benzyloxy-3-tert-Bu)-OMe in 60 ml of methanol and 20 ml of water was added 1.07 g (25.5 mmol) of lithium hydroxide monohydrate, and the mixture was stirred at room temperature for 1.5 hours. The reaction solution was neutralized with 2N hydrochloric acid with ice cooling, and then acidified with 10% aqueous citric acid. The reaction solution was extracted with methylene chloride and dried over anhydrous magnesium sulfate, and then concentrated under reduced pressure to give 6.8 g (93%) of crude Boc-Phe (4-benzyloxy-3-tert-Bu)-OH.

To a mixed solution of 6.2 g (14.5 mmol) of the crude compound in 30 ml of THF and 3 ml of DMF were added 7.2 ml (116 mmol) of methyl iodide with ice cooling, then 1.74 g (43.5 mmol) of 60% sodium hydride. The mixture was stirred at room temperature for 21 hours, and then stirred with 0.58 g (14.5 mmol) of 60% sodium hydride and 2.7 ml (43.5 mmol) of methyl iodide for 7 hours. The reaction solution was combined with water with ice cooling and washed with a mixed solution of n-hexane (150 ml)-ether (50 ml). The aqueous layer was neutralized with 2N hydrochloric acid with ice cooling, acidified with 10% aqueous citric acid solution, and then extracted with ethyl acetate. The extract was successively washed with water and saturated aqueous sodium chloride solution, and then dried over anhydrous magnesium sulfate and concentrated under reduced pressure to give 5.0 g (78%) of a crude product of the title compound.

(3) Synthesis of Boc-N-Me-Phe (4-benzyloxy-3-tert-Bu)-β-Ala-OBzl

To a solution of 2.68 g (6.08 mmol) of the crude Boc-N-Me-Phe (4-benzyloxy-3-tert-Bu)-OH and 2.35 g (6.69 mmol) of H-β-Ala-OBzl p-toluenesulfonate in 20 ml of DMF were added 0.82 g (6.08 mmol) of HOBt, 0.69 ml (6.08 mmol) of NMM and 1.28 g (6.69 mmol) of WSCI with ice cooling, and the mixture was stirred overnight at room temperature. The reaction solution was combined with water and then 10% aqueous citric acid solution, and then extracted with ethyl acetate. The organic layer was washed with saturated aqueous NaHCO$_3$ solution and saturated aqueous sodium chloride solution and dried over magnesium sulfate, and then the solvent was distilled off under reduced pressure to give 3.70 g (quant.) of the title compound.

(4) Synthesis of N-Me-Phe (4-benzyloxy-3-tert-Bu)-β-Ala-OBzl

To a solution of 3.64 g (6.03 mmol) of Boc-N-Me-Phe (4-benzyloxy-3-tert-Bu)-β-Ala-OBzl in 20 ml of methylene chloride was added 10 ml of TFA, and the mixture was stirred at room temperature for 45 minutes. The reaction solution was concentrated under reduced pressure, and the residue was neutralized with saturated aqueous NaHCO$_3$ solution, and then extracted with methylene chloride and the extract was washed with saturated aqueous sodium chloride solution. The organic layer was dried over magnesium sulfate, and then the solvent was distilled off under reduced pressure to give 3.02 g (99%) of the title compound.

(5) Synthesis of Boc-N-Me-Lys (Z)-N-Me-Phe (4-benzyloxy-3-tert-Bu)-β-Ala-OBzl

To a solution of 3.00 g (5.96 mmol) of N-Me-Phe (4-benzyloxy-3-tert-Bu)-β-Ala-OBzl, 4.12 g (7.16 mmol) of Boc-N-Me-Lys (Z)-OH dicyclohexylamine salt and 1.98 g (7.75 mmol) of CMPI in 30 ml of THF was added 2.91 ml (20.9 mmol) of TEA, and the mixture was stirred overnight at room temperature. The reaction solution was combined with water and extracted with ethyl acetate, and the extract was successively washed with 10% aqueous citric acid solution, saturated aqueous NaHCO$_3$ solution and saturated aqueous sodium chloride solution. The organic layer was dried over magnesium sulfate, and then concentrated under reduced pressure, and the residue was purified by silica gel column chromatography (developing solvent; ethyl acetate:n-hexane= 1:1) to give 2.95 g (56%) of the title compound.

(6) Synthesis of Boc-Phe (4-F)-N-Me-Lys (Z)-N-Me-Phe (4-benzyloxy-3-tert-Bu)-β-Ala-OBzl To a solution of 2.90 g (3.30 mmol) of Boc-N-Me-Lys (Z)-N-Me-Phe (4-benzyloxy-3-tert-Bu)-β-Ala-OBzl in 20 ml of methylene chloride was added 10 ml of TFA, and the mixture was stirred at room temperature for 45 minutes. The reaction solution was concentrated under reduced pressure, and the residue was neutralized with saturated aqueous NaHCO$_3$ solution, and then extracted with methylene chloride. The organic layer was dried over magnesium sulfate, and then the solvent was distilled off under reduced pressure to give 2.53 g (98%) of crude N-Me-Lys (Z)-N-Me-Phe (4-benzyloxy-tert-Bu)-β-Ala-OBzl.

To a solution of 2.50 g (3.21 mmol) of the crude compound, 1.00 g (3.53 mmol) of Boc-Phe (4-F)-OH and 0.98 g (3.85 mmol) of CMPI in 16 ml of THF was added 0.98 ml (7.06 mmol) of TEA with ice cooling, and the mixture was stirred overnight at room temperature. The reaction solution was combined with water and extracted with ethyl acetate, and the extract was successively washed with 10% aqueous citric acid solution, saturated aqueous NaHCO$_3$ solution and saturated aqueous sodium chloride solution. The organic layer was dried over magnesium sulfate, and then concentrated under reduced pressure, and the residue was purified by silica gel column chromatography (developing solvent; ethyl acetate:hexane=2:1) to give 3.00 g (89%) of the title compound.

(7) Synthesis of (2S-(2S,13S))-2-tert-butoxycarbonylamino-N-(2-(3-tert-butyl-4-hydroxyphenylmethyl)-1-methyl-1,4,8-triaza-3,7,14-trioxocyclotetradec-13-yl)-3-(4-fluorophenyl)-N-methylpropionamide To a solution of 2.72 g (2.60 mmol) of Boc-Phe (4-F)-pN-Me-Lys (Z)-N-Me-Phe (4-benzyloxy-3-tert-Bu)-β-Ala-OBzl in 50 ml of methanol was added 0.60 g of palladium hydroxide on carbon, and the mixture was stirred overnight at room temperature under a hydrogen atmosphere. After the reaction solution was filtered, the filtrate was concentrated under reduced pressure to give 1.98 g of crude Boc-Phe (4-F)-N-Me-Lys-N-Me-Tyr (3-tert-Bu)-β-Ala-OH.

To a mixed solution of 1.98 g (2.60 mmol) of the crude compound in 130 ml of DMF and 130 ml of pyridine was added 3.45 g (7.80 mmol) of BOP reagent, and the mixture was stirred at room temperature for 26 hours. The reaction solution was concentrated under reduced pressure, combined with water and extracted with ethyl acetate. The organic layer was successively washed with 10% aqueous citric acid solution, saturated aqueous NaHCO$_3$ solution and saturated aqueous sodium chloride solution, and then dried over magnesium sulfate and concentrated under reduced pressure. The residue was purified by silica gel column chromatography (developing solvent; methylene chloride:methanol:aqueous ammonia=20:1:0.1) to give 0.66 g (36%, 2 steps) of the title compound.

(8) Synthesis of (2S-(2S,13S))-2-amino-N-(2-(3-tert-butyl-4-hydroxyphenylmethyl)-1-methyl-1,4,8-triaza-3,7,14-trioxocyclotetradec-13-yl)-3-(4-fluorophenyl)-N-methylpropionamide To a solution of 0.60 g (0.843 mmol) of (2S-(2S,13S))-2-tert-butoxycarbonylamino-N-(2-(3-tert-butyl-4-hydroxyphenylmethyl)-1-methyl-1,4,8-triaza-3,7,14-trioxocyclotetradec-13-yl)-3-(4-fluorophenyl)-N-methylpropionamide in 10 ml of methylene chloride was added 3 ml of TFA, and the mixture was stirred at room temperature for 1 hour. The reaction solution was concentrated under reduced pressure, and the residue was neutralized with saturated aqueous NaHCO$_3$ solution and extracted with methylene chloride. The organic layer was dried over magnesium sulfate, and then the solvent was distilled off under reduced pressure, and the residue was dissolved in 8 ml of methanol with heating. Crystals precipitated at room temperature were filtered off to give 265 mg (51%) of the title compound.

FAB-MS (M$^+$+1): 612. $^1$H-NMR (DMSO-d): δ 1.0–1.5 (6H, m), 1.28 (9H, s), 2.0–2.3 (3H, m), 2.4–2.7 (2H, m), 2.48 and 2.64 (total 3H, s), 2.9–3.1 (4H, m), 3.5–3.7 (2H, m), 5.22 (1H, d, J=10.9 Hz), 5.33 (1H, t, J=7.3 Hz), 6.5–6.7 (2H, m), 6.9–7.1 (4H, m), 7.1–7.2 (2H, m), 7.7–7.8 (1H, m), 8.97 (1H, s).

Example 3

(2S-(2S,12S))-2-amino-N-(2-(3-tert-butyl-4-hydroxyphenylmethyl)-1,4,8-triaza-3,7,13-trioxocyclotridec-12-yl)-3-(4-fluorophenyl)-N-methylpropionamide

(1) Synthesis of Boc-Tyr (3-tert-Bu)-Gly-OBzl

To a solution of 2.30 g (6.81 mmol) of Boc-Tyr (3-tert-Bu)-OH and 1.51 g (7.50 mmol) of H-Gly-OBzl hydrochloride in 20 ml of DMF were added 0.92 g (6.81 mmol) of HOBt, 0.78 ml (6.81 mmol) of NMM and 1.44 g (7.50 mmol) of WSCI with ice cooling, and the mixture was stirred at room temperature for 105 minutes. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure, and the residue was purified by silica gel column chromatography (developing solvent; ethyl acetate:n-hexane=1:2) to give 1.57 g (48%) of the title compound.

(2) Synthesis of Boc-N-Me-Lys (Z)-Tyr (3-tert-Bu)-Gly-OBzl

To a solution of 1.52 g (3.14 mmol) of Boc-Tyr (3-tert-Bu)-Gly-OBzl in 25 ml of methylene chloride was added 8 ml of TFA, and the mixture was stirred at room temperature for 75 minutes. The reaction solution was concentrated under reduced pressure, and the residue was neutralized with saturated aqueous NaHCO$_3$ solution, and then extracted with methylene chloride, and the extract was washed with saturated aqueous sodium chloride solution. The organic layer was dried over magnesium sulfate, and then the solvent was distilled off under reduced pressure to give 1.19 g (98%) of crude H-Tyr (3-tert-Bu)-Gly-OBzl.

To a solution of 1.15 g (2.99 mmol) of the crude compound and 1.89 g (3.29 mmol) of Boc-N-Me-Lys (Z)-OH dicyclohexylamine salt in 20 ml of DMF were added 0.40 g (2.99 mmol) of HOBt, 0.34 ml (2.99 mmol) of NMM and 0.63 g (3.29 mmol) of WSCI with ice cooling, and the mixture was stirred at room temperature for 2.5 hours. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure, and the residue was purified by silica gel column chromatography (developing solvent; ethyl acetate:n-hexane=2:1) to give 2.16 g (95%) of the title compound.

(3) Synthesis of Boc-Phe (4-F)-N-Me-Lys (Z)-Tyr (3-tert-Bu)-Gly-OBzl

To a solution of 2.12 g (2.79 mmol) of Boc-N-Me-Lys (Z)-Tyr (3-tert-Bu)-Gly-OBzl in 24 ml of methylene chloride was added 8 ml of TFA, and the mixture was stirred at room temperature for 1 hour. The reaction solution was concentrated under reduced pressure, and the residue was neutralized with saturated aqueous NaHCO$_3$ solution, and then extracted with methylene chloride. The organic layer was dried over magnesium sulfate, and then the solvent was distilled off under reduced pressure to give 1.81 g of crude N-Me-Lys (Z)-Tyr (3-tert-Bu)-Gly-OBzl.

To a solution of 1.79 g (2.71 mmol) of the crude compound, 0.84 g (2.98 mmol) of Boc-Phe (4-F)-OH and 0.83 g (3.25 mmol) of CMPI in 13 ml of THF was added 0.83 ml (5.96 mmol) of TEA with ice cooling, and the mixture was stirred overnight at room temperature. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then concentrated under reduced pressure, and the residue was purified by silica gel column chromatography (developing solvent; methylene chloride:methanol:aqueous ammonia=50:1:0.05) to give 2.34 g (90%, 2 steps) of the title compound.

(4) Synthesis of (2S-(2S,12S))-2-tert-butoxycarbonylamino-N-(2-(3-tert-butyl-4-hydroxyphenylmethyl)-1,4,8-triaza-3,7,13-trioxocyclotridec-12-yl)-3-(4-fluorophenyl)-N-methylpropionamide To a solution of 1.99 g (2.15 mmol) of Boc-Phe (4-F)-pN-Me-Lys (Z)-Tyr (3-tert-Bu)-Gly-OBzl in 40 ml of methanol was added 0.40 g of palladium hydroxide on carbon, and the mixture was stirred overnight at room temperature under a hydrogen atmosphere. The reaction solution was filtered, and then the filtrate was concentrated under reduced pressure to give 1.60 g of crude Boc-Phe (4-F)-N-Me-Lys-Tyr (3-tert-Bu)-Gly-OH.

To a mixed solution of 1.60 g (2.15 mmol) of the crude compound in 100 ml of DMF and 100 ml of pyridine was added 2.85 g (6.45 mmol) of BOP reagent, and the mixture was stirred at room temperature for 23 hours. The reaction solution was concentrated under reduced pressure, combined with water, and extracted with ethyl acetate. The organic layer was successively washed with 10% aqueous citric acid solution and saturated aqueous sodium chloride solution, and then dried over magnesium sulfate, and concentrated under reduced pressure. The residue was purified by silica gel column chromatography (developing solvent; methylene chloride:methanol:aqueous ammonia=25:1:0.05) to give 0.88 g (60%, 2 steps) of the title compound.

(5) Synthesis of (2S-(2S,12S))-2-amino-N-(2-(3-tert-butyl-4-hydroxyphenylmethyl)-1,4,8-triaza-3,7,13-trioxocyclotridec-12-yl)-3-(4-fluorophenyl)-N-methylpropionamide To a solution of 0.86 g (1.26 mmol) of (2S-(2S,12S))-2-tert-butoxycarbonylamino-N-(2-(3-tert-butyl-4-hydroxyphenylmethyl)-1,4,8-triaza-3,7,13-trioxocyclotridec-12-yl)-3-(4-fluorophenyl)-N-methylpropionamide in 15 ml of methylene chloride was added 5 ml of TFA, and the mixture was stirred at room temperature for 1 hour. The reaction solution was concentrated under reduced pressure, and the residue was neutralized with aqueous ammonia and extracted with methylene chloride. The organic layer was dried over magnesium sulfate, and then the solvent was distilled off under reduced pressure, and the residue was heated with 4 ml of methanol. After standing at room temperature, solids were filtered off to give 474 mg (65%) of the title compound.

FAB-MS (M$^+$+1): 584. $^1$H-NMR (DMSO-d): δ 0.6–2.0 (6H, m), 1.30 (9H, m), 2.4–3.0 (6H, m), 2.58 and 2.78 (total 3H, s), 3.2–3.5 (2H, m), 3.6–4.4 (3.5H, m), 4.9–5.0 (0.5H, m), 6.6–7.2 (8H, m), 8.6–8.8 (1H, m), 8.87 (0.5H, d, J=7.3 Hz), 9.00 and 9.05 (total 1H, s), 9.17 (0.5H, d, J=7.3 Hz).

Example 4

Synthesis of (2S-(2S,13S))-2-amino-N-(2-(3-tert-butyl-4-hydroxyphenylmethyl)-4-methyl-1,4,8-triaza-3,7,14-trioxocyclotetradec-13-yl)-3-(4-fluorophenyl)-N-methylpropionamide (1) Synthesis of Boc-Tyr (3-tert-Bu)-N-Me-β-Ala-OBzl To a solution of 2.41 g (7.15 mmol) of Boc-Tyr (3-tert-Bu)-OH and 1.66 g (8.58 mmol) of N-Me-β-Ala-OBzl (Chem. Pharm. Bull., 31, 10, 1983, 3553–3561) in 22 ml of DMF were added 966 mg (7.15 mmol) of HOBt, 0.817 ml (7.15 mmol) of NMM and 1.51 g (7.87 mmol) of WSCI with ice cooling, and the mixture was stirred at room temperature for 150 minutes. The reaction solution was combined with water and extracted with ethyl acetate, and then the extract was washed with saturated aqueous NaHCO$_3$ solution and saturated aqueous sodium chloride solution. The organic layer was dried over magnesium sulfate, and then the solvent was distilled off under reduced pressure to give 3.52 g (96%) of Boc-Tyr (3-tert-Bu)-N-Me-β-Ala-OBzl.

$^1$H-NMR (CDCl$_3$): δ 1.34, 1.36, 1.37, 1.40 and 1.42 (total 18H, s), 2.00–3.60 (9H, m), 4.66–4.80 (1H, m), 5.09 and 5.10 (total 2H, s), 5.16–5.44 (2H, m), 6.40–7.04 (3H, m), 7.30–7.42 (5H, m).

(2) Synthesis of H-Tyr (3-tert-Bu)-N-Me-β-Ala-OBzl

To a solution of 3.44 g (6.72 mmol) of Boc-Tyr (3-tert-Bu)-N-Me-β-Ala-OBzl in 30 ml of methylene chloride was added 10 ml of TFA, and the mixture was stirred at room temperature for 50 minutes. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure to give 2.70 g (97%) of H-Tyr (3-tert-Bu)-N-Me-β-Ala-OBzl.

$^1$H-NMR (CDCl$_3$): δ 1.37 (9H, s), 2.16–3.14 (4H, m), 2.73 and 2.84 (total 3H, s), 3.40–3.70 (2H, m), 3.85 and 3.97 (total 1H, t, J=6.9 Hz), 5.08 and 5.10 (total 2H, s), 6.53 and 6.57 (total 1H, d, J=8.3 Hz), 6.80 (1H, dd, J=1.3, 8.3 Hz), 6.99 (1H, d, J=1.3 Hz), 7.30–7.44 (5H, m).

(3) Synthesis of Boc-N-Me-Lys (Z)-Tyr (3-tert-Bu)-N-Me-β-Ala-OBzl

To a solution of 2.50 g (6.07 mmol) of H-Tyr (3-tert-Bu)-N-Me-β-Ala-OBzl and 3.67 g (6.37 mmol) of Boc-N-Me-Lys (Z)-OH dicyclohexylamine salt in 18 ml of DMF were added 820 mg (6.07 mmol) of HOBt, 0.728 ml (6.37 mmol) of NMM and 1.28 g (6.68 mmol) of WSCI with ice cooling, and the mixture was stirred at room temperature for 2 hours. The reaction solution was combined with water and extracted with ethyl acetate, and then the extract was successively washed with saturated aqueous NaHCO$_3$ solution and saturated aqueous sodium chloride solution. The organic layer was dried over magnesium sulfate, and then the solvent was distilled off under reduced pressure to give 4.17 g (87%) of Boc-N-Me-Lys (Z)-Tyr (3-tert-Bu)-N-Me-β-Ala-OBzl.

$^1$H-NMR (CDCl$_3$): δ 1.20–1.60 (5H, m), 1.36 (9H, s), 1.46 (9H, s), 1.78–1.92 (1H, m), 2.10–2.94 (4H, m), 2.61, 2.71 and 2.82 (total 6H, s), 3.17 (2H, q, J=6.6 Hz), 4.28–4.64 (2H, m), 4.40–5.48 (3H, m), 5.09 and 5.10 (total 4H, s), 6.50 and 6.57 (total 1H, d, J=7.9–8.2 Hz), 6.68 (1H, brs), 6.80–6.90 (1H, m), 7.01 (1H, s), 7.28–7.42 (10H, m).

(4) Synthesis of N-Me-Lys (Z)-Tyr (3-tert-Bu)-N-Me-β-Ala-OBzl

To a solution of 4.02 g (5.10 mmol) of Boc-N-Me-Lys (Z)-Tyr (3-tert-Bu)-N-Me-β-Ala-OBzl in 25 ml of methylene chloride was added 10 ml of TFA, and the mixture was stirred at room temperature for 40 minutes. The reaction solution was distilled off under reduced pressure, and the residue was neutralized with saturated aqueous NaHCO$_3$ solution, extracted with chloroform and the extract was washed with saturated aqueous sodium chloride solution.

The organic layer was dried over magnesium sulfate, and then the solvent was distilled off under reduced pressure to give 3.51 g (96%) of N-Me-Lys (Z)-Tyr (3-tert-Bu)-N-Me-β-Ala-OBzl.

$^1$H-NMR (CDCl$_3$): δ 0.90–1.04 (2H, m), 1.20–1.60 (4H, m), 1.38 (9H, s), 2.30 (3H, s), 2.54–3.16 (7H, m), 2.81 and 2.89 (total 3H, s), 3.50–3.80 (2H, m), 4.89 (1H, brs), 5.04–5.20 (1H, m), 5.11 and 5.13 (total 4H, s), 6.60–7.08 (4H, m), 7.28–7.40 (10H, m).

(5) Synthesis of Boc-Phe (4-F)-N-Me-Lys (Z)-Tyr (3-tert-Bu)-N-Me-β-Ala-OBzl

To a solution of 3.40 g (4.94 mmol) of N-Me-Lys (Z)-Tyr (3-tert-Bu)-N-Me-β-Ala-OBzl and 1.47 g (5.19 mmol) of Boc-Phe (4-F)-OH in 25 ml of THF were added 1.39 g (5.43 mmol) of CMPI and 1.51 ml (10.9 mmol) of TEA with ice cooling, and the mixture was stirred at room temperature for 2 hours. The reaction solution was combined with water, extracted with ethyl acetate and the extract was washed with saturated aqueous sodium chloride solution. The organic layer was dried over magnesium sulfate, and then the solvent was distilled off under reduced pressure, and the residue was purified by silica gel column chromatography (developing solvent; ethyl acetate:hexane=1:1) to give 4.22 g (90%) of Boc-Phe (4-F)-N-Me-Lys (Z)-Tyr (3-tert-Bu)-N-Me-β-Ala-OBzl.

$^1$H-NMR (CDCl$_3$): δ 0.80–1.90 (6H, m), 1.35 and 1.37 (total 18H, s), 2.36–3.66 (16H, m), 4.60–5.40 (5H, m), 5.08 and 5.11 (total 4H, s), 6.30–7.22 (7H, m), 7.30–7.42 (10H, m).

(6) Synthesis of (2S-(2S,13S))-2-tert-butoxycarbonylamino-N-(2-(3-tert-butyl-4-hydroxyphenylmethyl)-4-methyl-1,4,8-triaza-3,7,14-trioxocyclotetradec-13-yl)-3-(4-fluorophenyl)-N-methylpropionamide To a solution of 4.00 g (4.19 mmol) of Boc-Phe (4-F)-N-Me-Lys (Z)-Tyr (3-tert-Bu)-N-Me-β-Ala-OBzl in 84 ml of methanol was added 400 mg of 10% palladium on carbon, and the mixture was stirred overnight at room temperature under a hydrogen atmosphere. After filtration, the filtrate was concentrated under reduced pressure to give 3.05 g (100%) of Boc-Phe (4-F)-N-Me-Lys-Tyr (3-tert-Bu)-N-Me-β-Ala-OH.

To a mixed solution of 2.25 g (3.09 mmol) of the thus obtained Boc-Phe (4-F)-N-Me-Lys-Tyr (3-tert-Bu)-N-Me-β-Ala-OH in 150 ml of DMF and 150 ml of pyridine was added 4.10 g (9.27 mmol) of BOP reagent, and the mixture was stirred at room temperature for 16 hours. The reaction solution was combined with water and extracted with ethyl acetate, and then the extract was successively washed with 10% aqueous CUSO$_4$ solution, saturated aqueous NaHCO$_3$ solution and saturated aqueous sodium chloride solution. The organic layer was dried over magnesium sulfate, and then the solvent was distilled off under reduced pressure, and the residue was purified by silica gel column chromatography (developing solvent; chloroform:methanol=20:1) to give 1.32 g (60%) of (2S-(2S,13S))-2-tert-butoxycarbonylamino-N-(2-(3-tert-butyl-4-hydroxyphenylmethyl)-4-methyl-1,4,8-triaza-3,7,14-trioxocyclotetradec-13-yl)-3-(4-fluorophenyl)-N-methylpropionamide.

$^1$H-NMR (CDCl$_3$): δ 1.20–2.02 (6H, m), 1.30, 1.33, 1.37, 1.38 and 1.47 (total 18H, s), 2.40–3.30 (16H, m), 3.60–3.78 (1H, m), 4.30–5.50 (4H, m), 6.50–7.40 (7H, m).

(7) Synthesis of (2S-(2S,13S))-2-amino-N-(2-(3-tert-butyl-4-hydroxyphenylmethyl)-4-methyl-1,4,8-triaza-3,7,14-trioxocyclotetradec-13-yl)-3-(4-fluorophenyl)-N-methylpropionamide To a solution of 1.20 g (1.69 mmol) of (2S-(2S,13S))-2-tert-butoxycarbonylamino-N-(2-(3-tert-butyl-4-hydroxyphenylmethyl)-4-methyl-1,4,8-triaza-3,7,14-trioxocyclotetradec-13-yl)-3-(4-fluorophenyl)-N-methylpropionamide in 15 ml of methylene chloride was added 5 ml of TFA, and the mixture was stirred at room temperature for 40 minutes. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol:aqueous ammonia=20:1:0.1) to give 1.08 g (92%) of the title compound.

FAB-MS (M$^+$+1): 612. $^1$H-NMR (DMSO-d): δ 0.50–3.40 (16H, m), 1.29 (9H, s), 2.74, 2.78 and 2.87 (total 6H, s), 3.77 and 4.42 (total 1H, t, J=6.5 Hz), 4.02–4.16 (1H, m), 4.88–5.04 (1H, m), 6.61 (1H, d, J=8.0 Hz), 6.78 (1H, dd, J=2.0, 8.0 Hz), 6.90–7.24 (4H, m), 7.40–7.56 (1H, m), 8.31 and 9.07 (total 1H, s), 8.40 and 8.79 (total 1H, d, J=8.9–9.2 Hz).

Example 5

Synthesis of (2S-(2S,13S))-2-amino-N-(2-(3-tert-butyl-4-hydroxyphenylmethyl)-8-methyl-1,4,8-triaza-3,7,14-trioxocyclotetradec-13-yl)-3-(4-fluorophenyl)-N-methylpropionamide (1) Synthesis of Boc-N-Me-Lys (Me, Z)-OH To a solution of 3.50 g (9.21 mmol) of Boc-Lys (Z)-OH in 86 ml of THF were added 1.37 g (34.3 mmol) of 60% sodium hydride and 4.27 ml (68.6 mmol) of methyl iodide with ice cooling, and the mixture was stirred at room temperature for 15 hours. The reaction solution was combined with 10% aqueous citric acid solution with ice cooling, extracted with ethyl acetate and the extract was washed with saturated aqueous sodium chloride solution. The organic layer was dried over magnesium sulfate, and then the solvent was distilled off under reduced pressure, and the residue was purified by silica gel column chromatography (developing solvent; ethyl acetate:n-hexane:=1:1) to give 3.60 g (96%) of Boc-N-Me-Lys (Me, Z)-OH.

$^1$H-NMR (CDCl$_3$): δ 1.20–2.02 (6H, m), 1.46 (9H, s), 2.79 (3H, s), 2.91 (3H, s), 3.22–3.34 (2H, m), 4.34–4.70 (1H, m), 5.12 (2H, s), 7.30–7.42 (5H, m).

(2) Synthesis of Boc-N-Me-Lys (Me, Z)-Tyr (3-tert-Bu)-β-Ala-OBzl

To a solution of 2.50 g (6.28 mmol) of H-Tyr (3-tert-Bu)-P-Ala-OBzl and 2.82 g (6.91 mmol) of Boc-N-Me-Lys (Me, Z)-OH in 18.8 ml of DMF were added 849 mg (6.28 mmol) of HOBt, 0.718 ml (6.28 mmol) of NMM and 1.32 g (6.91 mmol) of WSCI with ice cooling, and the mixture was stirred at room temperature for 90 minutes. The reaction solution was combined with water, extracted with ethyl acetate and the extract was washed with 10% aqueous citric acid solution, saturated aqueous NaHCO$_3$ solution and saturated aqueous sodium chloride solution. The organic layer was dried over magnesium sulfate, and then the solvent was distilled off under reduced pressure to give 4.81 g (97%) of Boc-N-Me-Lys (Me, Z)-Tyr (3-tert-Bu)-β-Ala-OBzl.

$^1$H-NMR (CDCl$_3$): δ 1.10–1.90 (6H, m), 1.37 (9H, s), 1.45 (9H, s), 2.40–2.60 (5H, m), 2.80–3.00 (2H, m), 2.88 and 2.96 (total 3H, s), 3.16–3.50 (4H, m), 4.30–4.58 (2H, m), 5.09 and 5.11 (total 4H, s), 6.30–6.68 (3H, m), 6.83 (1H, dd, J=1.7, 7.9 Hz), 7.03 (1H, d, J=1.7 Hz), 7.30–7.42 (10H, m).

(3) Synthesis of N-Me-Lys (Me, Z)-Tyr (3-tert-Bu)-β-Ala-OBzl

To a solution of 4.48 g (5.69 mmol) of Boc-N-Me-Lys (Me, Z)-Tyr (3-tert-Bu)-β-Ala-OBzl in 30 ml of methylene chloride was added 10 ml of TFA, and the mixture was stirred at room temperature for 40 minutes. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure to give 3.80 g (97%) of N-Me-Lys (Me, Z)-Tyr (3-tert-Bu)-β-Ala-OBzl.

$^1$H-NMR (CDCl$_3$): δ 0.70–1.60 (6H, m), 1.38 (9H, s), 2.29 (3H, s), 2.50–2.62 (2H, m), 2.68–2.90 (3H, m), 2.88 and 2.96 (total 3H, s), 3.14–3.60 (4H, m), 4.40–4.70 (1H, m), 5.12 and 5.18 (total 4H, s), 6.60–6.90 (3H, m), 7.02 (1H, s), 7.30–7.42 (10H, m).

(4) Synthesis of Boc-Phe (4-F)-N-Me-Lys (Me, Z)-Tyr (3-tert-Bu)-β-Ala-OBzl

To a solution of 3.51 g (5.10 mmol) of N-Me-Lys (Me, Z)-Tyr (3-tert-Bu)-β-Ala-OBzl and 1.52 g (5.36 mmol) of Boc-Phe (4-F)-OH in 25.5 ml of THF were added 1.43 g (5.61 mmol) of CMPI and 1.56 ml (11.2 mmol) of TEA with ice cooling, and the mixture was stirred at room temperature for 90 minutes. The reaction solution was combined with water and extracted with ethyl acetate, and then the extract was washed with saturated aqueous sodium chloride solution. The organic layer was dried over magnesium sulfate, and then the solvent was distilled off under reduced pressure, and the residue was purified by silica gel column chromatography (developing solvent; ethyl acetate:hexane=1:1) to give 4.59 g (94%) of Boc-Phe (4-F)-N-Me-Lys (Me, Z)-Tyr (3-tert-Bu)-β-Ala-OBzl.

$^1$H-NMR (CDCl$_3$): δ 0.90–1.40 (5H, m), 1.30, 1.36 and 1.39 (total 18H, s), 1.76–1.92 (1H, m), 2.10–3.60 (16H, m), 4.40–4.80 (2H, m), 4.99, 5.11 and 5.13 (total 4H, s), 5.00–5.60 (2H, m), 6.50–7.40 (18H, m).

(5) Synthesis of (2S-(2S,13S))-2-(tert-butoxycarbonylamino)-N-( 2-(3-tert-butyl-4-hydroxyphenylmethyl)-8-methyl-1,4,8-triaza-3,7,14-trioxocyclotetradec-13-yl)-3-(4-fluorophenyl)-N-methylpropionamide To a solution of 4.32 g (4.53 mmol) of Boc-Phe (4-F)-pN-Me-Lys (Me, Z)-Tyr (3-tert-Bu)-β-Ala-OBzl in 50 ml of methanol was added 400 mg of 10% palladium on carbon, and the mixture was hydrogen at room temperature for 4 hours under a hydrogen atmosphere. After filtration, the filtrate was concentrated under reduced pressure to give 3.32 g (100%) of Boc-Phe (4-F)-N-Me-Lys (Me)-Tyr (3-tert-Bu)-β-Ala-OH.

To a mixed solution of 2.30 g (3.16 mmol) of the thus obtained Boc-Phe (4-F)-N-Me-Lys (Me)-Tyr (3-tert-Bu)-β-Ala-OH in 150 ml of DMF and 150 ml of pyridine was added 4.19 g (9.48 mmol) of BOP reagent, and the mixture was stirred at room temperature for 16 hours. The reaction solution was combined with water, extracted with ethyl acetate and the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol=20:1) to give 811 mg (36%) of (2S-(2S,13S))-2-(tert-butoxycarbonylamino)-N-(2-(3-tert-butyl-4-hydroxyphenylmethyl)-8-methyl-1,4, 8-triaza-3,7,14-trioxocyclotetradec-13-yl)-3-(4-fluorophenyl)-N-methylpropionamide.

$^1$H-NMR (CDCl$_3$): δ 0.80–2.00 (6H, m), 1.34, 1.37 and 1.40 (total 18H, s), 2.30–3.40 (16H, m), 4.40–4.70 (2H, m), 5.16–5.44 (2H, m), 6.40–7.20 (9H, m).

(6) Synthesis of (2S-(2S,13S))-2-amino-N-(2-(3-tert-butyl-4-hydroxyphenylmethyl)-8-methyl-1,4,8-triaza-3,7,14-trioxocyclotetradec-13-yl)-3-(4-fluorophenyl)-N-methylpropionamide To a solution of 748 mg (1.05 mmol) of (2S-(2S,13S))-2-(tert-butoxycarbonylamino)-N-(2-(3-tert-butyl-4-hydroxyphenylmethyl)-8-methyl-1,4,8-triaza-3,7,14-trioxocyclotetradec-13-yl)-3-(4-fluorophenyl)-N-methylpropionamide in 10 ml of methylene chloride was added 5 ml of TFA, and the mixture was stirred at room temperature for 40 minutes. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol=20:1) to give 608 mg (95%) of the title compound.

FAB-MS (M$^+$+1): 612. $^1$H-NMR (DMSO-d): δ 0.60–1.90 (6H, m), 1.26 and 1.28 (total 9H, s), 2.20–2.90 (12H, m), 3.20–4.40 (6H, m), 4.80–4.90 (1H, m), 6.61 (1H, d, J=7.9 Hz), 6.70–7.60 (7H, m), 8.08–8.60 (1H, m), 9.01 and 9.11 (total 1H, s).

Example 6

Synthesis of (2S-(2S,14S))-2-amino-N-(2-(3-tert-butyl-4-hydroxyphenylmethyl)-1,4,9-triaza-3,8,15-trioxocyclopentadec-14-yl)-3-(4-fluorophenyl)-N-methylpropionamide (1) Synthesis of N-(Boc-3-tert-Bu-tyrosyl)-4-aminobutyric acid benzyl ester To a solution of 2.01 g (5.96 mmol) of Boc-Tyr (3-tert-Bu)-OH and 1.51 g (6.56 mmol) of 4-aminobutyric acid benzyl ester hydrochloride (Helv. Chim. Acta., 80, 1997, 1253) in 24 ml of DMF were added 805 mg (5.96 mmol) of HOBt, 0.750 ml (6.56 mmol) of NMM and 1.26 g (6.57 mmol) of WSCI with ice cooling, and the mixture was stirred at room temperature for 90 minutes. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure to give 2.49 g (82%) of N-(Boc-3-tert-Bu-tyrosyl)-4-aminobutyric acid benzyl ester.

$^1$H-NMR (CDCl$_3$): δ 1.37 (9H, s), 1.41 (9H, s), 1.62–1.78 (2H, m), 2.26 (2H, t, J=7.3 Hz), 2.82–3.30 (4H, m), 4.20 (1H, q, J=7.3 Hz), 4.97 (1H, brs), 5.10 (2H, s), 5.83 (1H, brs), 6.54 (1H, d, J=7.9 Hz), 6.86 (1H, dd, J=1.7, 7.9 Hz), 7.04 (1H, d, J=1.7 Hz), 7.30–7.42 (5H, m).

(2) Synthesis of N-(3-tert-Bu-tyrosyl)-4-aminobutyric acid benzyl ester

To a solution of 2.42 g (4.73 mmol) of N-(Boc-3-tert-Bu-tyrosyl)-4-aminobutyric acid benzyl ester in 20 ml of methylene chloride was added 5 ml of TFA, and the mixture was stirred at room temperature for 1 hour. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure to give 1.94 g (100%) of N-(3-tert-Bu-tyrosyl)-4-aminobutyric acid benzyl ester.

$^1$H-NMR (CDCl$_3$): δ 1.39 (9H, s), 1.85 (2H, tt, J=6.6, 7.6 Hz), 2.38 (2H, t, J=7.6 Hz), 2.60 (1H, dd, J=9.2, 13.8 Hz), 3.14 (1H, dd, J=3.9, 13.8 Hz), 3.30 (2H, q, J=6.6 Hz), 3.53 (1H, dd, J=3.9, 9.2 Hz), 5.12 (2H, s), 6.61 (1H, d, J=7.9 Hz), 6.88 (1H, dd, J=2.0, 7.9 Hz), 7.07 (1H, d, J=2.0 Hz), 7.30–7.42 (5H, m).

(3) Synthesis of N-(Boc-N-Me-Nϵ-Z-lysyl-3-tert-Bu-tyrosyl)-4-aminobutyric acid benzyl ester To a solution of 1.89 g (4.59 mmol) of N-(3-tert-Bu-tyrosyl)-4-aminobutyric acid benzyl ester and 2.78 g (4.82 mmol) of Boc-N-Me-Lys (Z)-OH in 14 ml of DMF were added 620 mg (4.59 mmol) of HOBt, 0.787 ml (6.89 mmol) of NMM and 968 mg (5.05 mmol) of WSCI with ice cooling, and the mixture was stirred at room temperature for 90 minutes. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure to give 3.41 g (90%) of N-(Boc-N-Me-Nϵ-Z-lysyl-3-tert-Bu-tyrosyl)-4-aminobutyric acid benzyl ester.

$^1$H-NMR (CDCl$_3$): δ 1.12–1.90 (8H, m), 1.36 (9H, s), 1.44 (9H, s), 2.27 (2H, t, J=7.3 Hz), 2.56 (3H, s), 2.90–3.30 (6H, m), 4.37 (1H, t, J=7.1 Hz), 4.69 (1H, q, J=7.6 Hz), 4.82 (1H, brs), 5.09 (4H, s), 5.50–5.70 and 6.00–6.20 (total 1H, m), 6.47 (1H, d, J=4.3 Hz), 6.59 (1H, d, J=7.9 Hz), 6.84 (1H, dd, J=1.7, 7.9 Hz), 7.04 (1H, d, J=1.7 Hz), 7.30–7.44 (10H, m).

(4) Synthesis of N-(N-Me-Nϵ-Z-lysyl-3-tert-Bu-tyrosyl)-4-aminobutyric acid benzyl ester To a solution of 3.32 g (4.21 mmol) of N-(Boc-N-Me-Nϵ-Z-lysyl-3-tert-Bu-tyrosyl)-4-aminobutyric acid benzyl ester in 20 ml of methylene chloride was added 10 ml of TFA, and the mixture was stirred at room temperature for 40 minutes. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure to give 2.86 g (99%) of N-(N-Me-Nϵ-Z-lysyl-3-tert-Bu-tyrosyl)-4-aminobutyric acid benzyl ester.

$^1$H-NMR (CDCl$_3$): δ 0.80–0.98 (2H, m), 1.10–1.70 (4H, m), 1.38 (9H, s), 1.81 (2H, tt, J=6.6, 7.3 Hz), 2.28 (3H, s), 2.35 (2H, t, J=7.3 Hz), 2.76–3.20 (5H, m), 3.27 (2H, q, J=6.6 Hz), 4.46–4.58 (1H, m), 4.80–4.94 (1H, m), 5.11 and 5.14 (total 4H, s), 6.40–6.52 (1H, m), 6.69 (1H, d, J=7.9 Hz), 6.84 (1H, dd, J=1.6, 7.9 Hz), 6.88 (1H, brs), 7.04 (1H, d, J=1.6 Hz), 7.30–7.46 (10H, m).

(5) Synthesis of N-(Boc-4-fluorophenylalanyl-N-Me-Nϵ-Z-lysyl-3-tert-Bu-tyrosyl)-4-aminobutyric acid benzyl ester To a solution of 2.82 g (4.10 mmol) of N-(N-Me-Nϵ-Z-lysyl-3-tert-Bu-tyrosyl)-4-aminobutyric acid benzyl ester and 1.28 g (4.51 mmol) of Boc-Phe (4-F)-OH in 21 ml of THF were added 1.26 g (4.92 mmol) of CMPI and 1.14 ml (8.20 mmol) of TEA with ice cooling, and the mixture was stirred at room temperature for 2 hours. The reaction solution was combined with water and extracted with ethyl acetate, and then the extract was washed with saturated aqueous sodium chloride solution. The organic layer was dried over magnesium sulfate, and then the solvent was distilled off under reduced pressure, and the residue was purified by silica gel column chromatography (developing solvent; ethyl acetate:hexane=1:1) to give 3.57 g (91%) of N-(Boc-4-fluorophenylalanyl-N-Me-Nϵ-Z-lysyl-3-tert-Bu-tyrosyl)-4-aminobutyric acid benzyl ester.

$^1$H-NMR (CDCl$_3$): δ 0.80–1.50 (6H, m), 1.35, 1.37 and 1.38 (total 18H, s), 1.70–1.86 (2H, m), 2.15 and 2.62 (total 3H, s), 2.24–2.38 (2H, m), 2.60–3.30 (8H, m), 4.28–4.94 (3H, m), 5.26–5.40 (1H, m), 6.08–7.20 (10H, m), 7.30–7.42 (10H, m).

(6) Synthesis of (2S-(2S,14S))-2-(tert-butoxycarbonylamino)-N-(2-(3-tert-butyl-4-hydroxyphenylmethyl)-1,4,9-triaza-3,8,15-trioxocyclopentadec-14-yl)-3-(4-fluorophenyl)-N-methylpropionamide To a solution of 3.50 g (3.67 mmol) of N-(Boc-4-fluorophenylalanyl-N-Me-Nϵ-Z-lysyl-3-tert-Bu-tyrosyl)-4-aminobutyric acid benzyl ester in 100 ml of methanol was added 400 mg of 10% palladium on carbon, and the mixture was stirred overnight at room temperature under a hydrogen atmosphere. After filtration, the filtrate was concentrated under reduced pressure to give 2.65 g (99%) of N-(Boc-4-fluorophenylalanyl-N-Me-lysyl-3-tert-Bu-tyrosyl)-4-aminobutyric acid.

To a mixed solution of 2.35 g (3.22 mmol) of the thus obtained N-(Boc-4-fluorophenylalanyl-N-Me-lysyl-3-tert-Bu-tyrosyl)-4-aminobutyric acid in 160 ml of DMF and 160 ml of pyridine was added 4.27 g (9.66 mmol) of BOP reagent, and the mixture was stirred at room temperature for 16 hours. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure, and the residue was purified by silica gel column chromatography (developing solvent; chloroform:methanol=20:1) to give 1.88 g (82%) of (2S-(2S,14S))-2-(tert-butoxycarbonylamino)-N-(2-(3-tert-butyl-4-hydroxyphenylmethyl)-1,4,9-triaza-3,8,15-trioxocyclopentadec-14-yl)-3-(4-fluorophenyl)-N-methylpropionamide.

$^1$H-NMR (CDCl$_3$): δ 1.04–1.50 (6H, m), 1.29, 1.34 and 1.39 (total 18H, s), 1.70–1.94 (2H, m), 2.10–2.40 (2H, m), 2.24 and 2.55 (total 3H, s), 2.56–3.70 (8H, m), 4.40–4.94 (3H, m), 5.24–5.40 (1H, m), 5.80–6.44 (2H, m), 6.62–7.20 (7H, m), 8.21 (1H, d, J=8.2 Hz).

(7) Synthesis of (2S-(2S,14S))-2-amino-N-(2-(3-tert-butyl-4-hydroxyphenylmethyl)-1,4,9-triaza-3,8,15-trioxocyclopentadec-14-yl)-3-(4-fluorophenyl)-N-methylpropionamide To a solution of 1.75 g (2.46 mmol) of (2S-(2S,14S))-2-(tert-butoxycarbonylamino)-N-(2-(3-tert-butyl-4-hydroxyphenylmethyl)-1,4,9-triaza-3,8,15-trioxocyclopentadec-14-yl)-3-(4-fluorophenyl)-N-methylpropionamide in 20 ml of methylene chloride was added 10 ml of TFA, and the mixture was stirred at room temperature for 40 minutes. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol:aqueous ammonia=20:1:0.1) to give 783 mg (52%) of the title compound.

FAB-MS (M$^+$+1): 612. $^1$H-NMR (DMSO-d): δ 0.60–2.00 (6H, m), 1.06 (2H, t, J=6.9 Hz), 1.28 and 1.29 (total 9H, s), 2.06–2.22 (2H, m), 2.50–3.00 (9H, m), 3.20–4.04 (3H, m), 4.24–4.44 (3/2H, m), 4.96 (1/2H, d, J=9.9 Hz), 6.61 (1H, d, J=8.3 Hz), 6.70–6.84 (1H, m); 6.90–7.74 (7H, m), 8.14 and 8.95 (total 1H, d, J=7.6–8.2 Hz), 9.04 and 9.09 (total 1H, s).

Example 7

Synthesis of (2S,14S)-13-(2S-2-amino-3-(4-fluorophenyl)propylamino)-2-(3-tert-butyl-4-hydroxyphenylmethyl)-1,4,8-triaza-3,7,14-trioxocyclotetradecane

(1) Synthesis of Z-Tyr (3-tert-Bu)-β-Ala-OtBu

To a solution of 2.69 g (7.25 mmol) of Z-Tyr (3-tert-Bu)-OH and 1.45 g (7.98 mmol) of H-β-Ala-OtBu hydrochloride in 22 ml of DMF were added 980 mg (7.25 mmol) of HOBt, 1.66 ml (14.5 mmol) of NMM and 1.53 g (7.98 mmol) of WSCI with ice cooling, and the mixture was stirred at room temperature for 90 minutes. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure to give 2.76 g (76%) of Z-Tyr (3-tert-Bu)-β-Ala-OtBu.

$^1$H-NMR (CDCl$_3$): δ 1.37 (9H, s), 1.41 (9H, s), 2.33 (2H, q, J=6.3 Hz), 2.88–3.06 (2H, m), 3.40 (2H, q, J=6.3 Hz), 4.20–4.34 (1H, m), 4.80–5.00 (1H, m), 5.09. (2H, s), 5.20–5.30 (1H, m), 6.12–6.24 (1H, m), 6.57 (1H, d, J=7.9 Hz), 6.86 (1H, d, J=7.9 Hz), 7.03 (1H, s), 7.30–7.42 (5H, m).

(2) Synthesis of H-Tyr (3-tert-Bu)-β-Ala-OtBu

To a solution of 2.70 g (5.42 mmol) of Z-Tyr (3-tert-Bu)-β-Ala-OtBu in 80 ml of methanol was added 300 mg of 10% palladium on carbon, and the mixture was stirred at room temperature for 5 hours under a hydrogen atmosphere. After filtration, the filtrate was concentrated under reduced pressure to give 1.96 g (99%) of H-Tyr (3-tert-Bu)-p-Ala-OtBu.

$^1$H-NMR (CDCl$_3$): δ 1.36 (9H, s), 1.43 (9H, s), 2.40 (2H, t, J=6.6 Hz), 2.77 (1H, dd, J=8.2, 13.5 Hz), 3.14 (1H, dd, J=4.6, 13.5 Hz), 3.36–3.50 (2H, m), 3.76–3.84 (1H, m), 6.71 (1H, d, J=7.9 Hz), 6.93 (1H, d, J=7.9 Hz), 7.04 (1H, s), 7.64–7.72 (1H, m).

(3) Synthesis of Z-N-Me-Lys (Boc)-Tyr (3-tert-Bu)-β-Ala-OtBu

To a solution of 1.90 g (5.22 mmol) of H-Tyr (3-tert-Bu)-β-Ala-OtBu and 2.18 g (5.74 mmol) of Z-N-Me-Lys (Boc)-OH in 17.5 ml of DMF were added 705 mg (5.22 mmol) of HOBt, 0.656 ml (5.74 mmol) of NMM and 1.10 g (8.14 mmol) of WSCI with ice cooling, and the mixture was stirred at room temperature for 1 hour. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure to give 3.49 g (92%) of Z-N-Me-Lys (Boc)-Tyr (3-tert-Bu)-β-Ala-OtBu.

$^1$H-NMR (CDCl$_3$): δ 0.90–1.10 (2H, m), 1.20–1.50 (4H, m), 1.37 (9H, s), 1.43 (9H, s), 1.44 (9H, s), 2.34–2.46 (2H, m), 2.80 (1H, dd, J=9.2, 14.2 Hz), 2.99 (2H, q, J=6.6 Hz), 3.10–3.24 (1H, m), 3.43 (2H, q, J=6.0 Hz), 3.94–4.04 (1H, m), 4.55 (1H, q, J=6.2 Hz), 4.65 (1H, brs), 5.10 (2H, s), 5.20–5.30 (1H, m), 6.34 (1H, d, J=6.0 Hz), 6.42 (1H, brs), 6.60 (1 h, brs), 6.66 (1H, d, J=7.9 Hz), 6.82 (1H, dd, J=1.7, 7.9 Hz), 7.01 (1H, d, J=1.7 Hz), 7.30–7.42 (5H, m).

(4) Synthesis of (2S,14S)-13-amino-2-(3-tert-butyl-4-hydroxyphenylmethyl)-1,4,8-triaza-3,7,14-trioxocyclotetradecane To a solution of 2.51 g (3.46 mmol) of Z-N-Me-Lys (Boc)-Tyr (3-tert-Bu)-β-Ala-OtBu in 10 ml of methylene chloride was added 10 ml of TFA, and the mixture was stirred at room temperature for 50 minutes. The reaction solution was distilled off under reduced pressure, and a mixed solution of the residue in 170 ml of acetonitrile and 170 ml of pyridine was stirred with 4.59 g (10.4 mmol) of BOP reagent at room temperature for 21 hours. The solvent was distilled off under reduced pressure, and the residue was successively washed with diethyl ether and chloroform to give solids. The thus obtained solids were dissolved in 50 ml of methanol and combined with 300 mg of 10% palladium on carbon, and the mixture was stirred overnight at room temperature under a hydrogen atmosphere. After filtration, the filtrate was concentrated under reduced pressure, and the residue was purified by silica gel column chromatography (developing solvent; chloroform:methanol aqueous ammonia=10:1:0.1) to give 1.30 g (90%) of (2S,14S)-13-amino-2-(3-tert-butyl-4-hydroxyphenylmethyl)-1,4,8-triaza-3,7,14-trioxocyclotetradecane.

$^1$H-NMR (CD$_3$OD): δ 0.90–1.40 (6H, m), 1.40 (9H, s), 2.28–2.50 (2H, m), 2.78 (1H, dd, J=7.6, 13.9 Hz), 3.06 (2H, dd, J=6.9, 13.5 Hz), 3.30–3.72 (4H, m), 4.65 (1H, t, J=7.6 Hz), 6.66 (1H, d, J=7.9 Hz), 6.90 (1H, dd, J=1.7, 7.9 Hz), 7.08 (1H, d, J=1.7 Hz).

(5) Synthesis of (2S,14S)-13-((2S)-2-(tert-butoxycarbonylamino)-3-(4-fluorophenyl)propylamino)-2-(3-tert-butyl-4-hydroxyphenylmethyl)-1,4,8-triaza-3,7,14-trioxocyclotetradecane To a solution of 0.89 g (2.13 mmol) of (2S,14S)-13-amino-2-(3-tert-butyl-4-hydroxyphenylmethyl)-1,4,8-triaza-3,7,14-trioxocyclotetradecane and 739 mg (2.77 mmol) of Boc-Phe (4-F)-H in 22 ml of methanol were added 1 ml of acetic acid and 423 mg (6.39 mmol) of 95% sodium cyanoborohydride with ice cooling, and the mixture was stirred at room temperature for 30 minutes. The reaction solution was combined with water and extracted with chloroform, and then the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol:aqueous ammonia=20:1:0.1) to give 793 mg (56%) of (2S,14S)-13-((2S)-2-(tert-butoxycarbonylamino)-3-(4-fluorophenyl)propylamino)-2-(3-tert-butyl-4-hydroxyphenylmethyl)-1,4,8-triaza-3,7,14-trioxocyclotetradecane.

$^1$H-NMR (CDCl$_3$): δ 1.12–1.80 (6H, m), 2.06 (1H, dd, J=5.3, 11.9 Hz), 2.18 (1H, dd, J=6.3, 11.9 Hz), 2.28–2.64 (3H, m), 2.70–2.80 (2H, m), 2.94–3.12 (3H, m), 3.42–3.68 (3H, m), 4.72 (1H, dd, J=6.3, 9.3 Hz), 6.65 (1H, d, J=7.9 Hz), 6.88 (1H, dd, J=2.0, 7.9 Hz), 7.00 (2 h, t, J=8.2 Hz), 7.11 (1H, d, J=2.0 Hz), 7.21 (2H, dd, J=7.6, 8.2 Hz).

(6) Synthesis of (2S,14S)-13-((2S)-2-amino-3-(4-fluorophenyl)propylamino)-2-(3-tert-butyl-4-hydroxyphenylmethyl)-1,4,8-triaza-3,7,14-trioxocyclotetradecane To a solution of 735 mg (1.10 mmol) of (2S,14S)-13-((2S)-2-(tert-butoxycarbonylamino)-3-(4-fluorophenyl)propylamino)-2-(3-tert-butyl-4-hydroxyphenylmethyl)-1,4,8-triaza-3,7,14-trioxocyclotetradecane in 5 ml of methylene chloride was added 3 ml of TFA, and the mixture was stirred at room temperature for 40 minutes. The reaction solution was distilled off under reduced pressure, and the residue was neutralized with saturated aqueous NaHCO$_3$ solution, extracted with chloroform and the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol:aqueous ammonia=5:1:0.1) to give 608 mg (97%) of the title compound.

FAB-MS (M$^+$+1): 570. $^1$H-NMR (DMSO-d): δ 1.00–1.52 (4H, m), 1.30 (9H, s), 1.64–1.94 (4H, m), 2.14–2.32 (3H, m), 2.50–2.90 (5H, m), 3.20–3.62 (4H, m), 4.42–4.56 (1H, m), 6.63 (1H, d, J=8.2 Hz), 6.77 (1H, d, J=8.2 Hz), 6.93 (1H, s), 7.00–7.24 (5H, m), 7.69 (1H, d, J=5.9 Hz), 8.09 (1H, d, J=9.2 Hz), 9.00–9.20 (1H, m).

Example 8

Synthesis of (2S-(2S.13S))-N-(8-acetyl-2-(3-tert-butyl-4-hydroxyphenylmethyl)-N-methyl-1,4,8-triaza-3,14-dioxocyclotetradec-13-yl)-2-amino-3-(4-fluorophenyl)propionamide (1) Synthesis of Boc-N-Me-Lys (Z)-Tyr (3-tert-Bu)-OMe To a solution of 2.00 g (7.97 mmol) of H-Tyr (3-tert-Bu)-OMe and 5.05 g (8.77 mmol) of Boc-N-Me-Lys (Z)-OH in 24 ml of DMF were added 1.08 g (7.97 mmol) of HOBt, 1.37 ml (12.0 mmol) of NMM and 1.68 g (8.77 mmol) of WSCI with ice cooling, and the mixture was stirred at room temperature for 3 hours. The reaction solution was combined with water and extracted with ethyl acetate, and then the extract was successively washed with 10% aqueous citric acid solution, saturated aqueous NaHCO$_3$ solution and saturated aqueous sodium chloride solution. The organic layer was dried over magnesium sulfate, and then the solvent was distilled off under reduced pressure, and the residue was purified by silica gel column chromatography (developing solvent; ethyl acetate:hexane 1:1) to give 4.99 g (100%) of Boc-N-Me-Lys (Z)-Tyr (3-tert-Bu)-OMe.

$^1$H-NMR (CDCl$_3$): δ 1.14–1.30 (2H, m), 1.37 (9H, s), 1.43 (9H, s), 1.40–1.64 (3H, m), 1.78–1.96 (1H, m), 2.56 (3H, s), 2.93 (1H, dd, J=7.3, 14.2 Hz), 3.04–3.22 (3H, m), 3.73 (3H, s), 4.44 (1H, t, J=7.6 Hz), 4.72–4.86 (2H, m), 5.09 (2H, s), 5.55 (1H, brs), 6.40 (1H, brs), 6.61 (1H, d, J=7.9 Hz), 6.77 (1 h, d, J=7.9 Hz), 6.95 (1H, s), 7.30–7.40 (5H, m).

(2) Synthesis of Boc-N-Me-Lys-Tyr (3-tert-Bu)-OMe

To a solution of 4.92 g (7.85 mmol) of Boc-N-Me-Lys (Z)-Tyr (3-tert-Bu)-OMe in 80 ml of methanol was added 500 mg of 10% palladium on carbon, and the mixture was stirred overnight at room temperature under a hydrogen atmosphere. After filtration, the filtrate was concentrated under reduced pressure to give 3.87 g (100%) of Boc-N-Me-Lys-Tyr (3-tert-Bu)-OMe.

$^1$H-NMR (CDCl$_3$): δ 1.20–1.94 (6H, m), 1.36 (9H, s), 1.43 (9H, s), 2.63 (3H, s), 2.80–3.00 (3H, m), 3.12 (1H, dd, J=5.0, 13.8 Hz), 3.74 (3H, s), 4.45 (1H, t, J=6.9 Hz), 4.70–4.80 (1H, m), 6.73 (1H, d, J=7.9 Hz), 6.82 (1H, d, J=7.9 Hz), 6.94 (1H, s).

(3) Synthesis of Boc-N-Me-Nε-(3-benzyloxycarbonylaminopropyl)-Lys-Tyr (3-tert-Bu)-OMe To a solution of 3.10 g (6.29 mmol) of Boc-N-Me-Lys-Tyr (3-tert-Bu)-OMe and 1.43 g (6.92 mmol) of N-phenyl-methoxycarbonyl-3-aminopropanal in 63 ml of methanol were added 0.36 ml of acetic acid and 832 mg (12.6 mmol) of 95% sodium cyanoborohydride with ice cooling, and the mixture was stirred at room temperature overnight. The reaction solution was combined with water and extracted with chloroform, and then the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol:aqueous ammonia=20:1:0.1) to give 2.30 g (53%) of Boc-N-Me-Nε-(3-benzyloxycarbonylaminopropyl)-Lys-Tyr (3-tert-Bu)-OMe.

¹H-NMR (CDCl₃): δ 1.16–2.00 (8H, m), 1.37 (9H, s), 1.44 (9H, s), 2.61 (3H, s), 2.72 (2H, t, J=7.3 Hz), 2.85 (2H, t, J=6.6 Hz), 2.84–2.94 (1H, m), 3.12 (1H, dd, J=5.3, 13.9 Hz), 3.24–3.38 (2H, m), 3.74 (3H, s), 4.42 (1H, t, J=7.3 Hz), 4.75 (1H, q, J=6.6 Hz), 5.10 (2H, s), 5.40–5.50 (1H, m), 6.56–6.66 (1H, m), 6.70 (1H, d, J=7.9 Hz), 6.78 (1H, dd, J=1.7, 7.9 Hz), 6.95 (1H, d, J=1.7 Hz), 7.28–7.40 (5H, m).

(4) Synthesis of Boc-N-Me-Nε-(3-benzyloxycarbonylaminopropyl)-Nε-acetyl-Lys-Tyr (3-tert-Bu)-OMe To a solution of 2.24 g (3.27 mmol) of Boc-N-Me-Nε-(3-benzyloxycarbonylaminopropyl)-Lys-Tyr (3-tert-Bu)-OMe in 33 ml of methylene chloride were added 0.401 ml (4.25 mmol) of acetic anhydride and 0.684 ml (4.91 mmol) of TEA with ice cooling, and the mixture was stirred for 30 minutes. The reaction solution was neutralized with saturated aqueous NaHCO₃ solution, extracted with methylene chloride and the extract was washed with saturated aqueous sodium chloride solution. The organic layer was dried over magnesium sulfate, and then the solvent was distilled off under reduced pressure, and the residue was purified by silica gel column chromatography (developing solvent; chloroform:methanol:aqueous ammonia=30:1:0.1) to give 1.92 g (81%) of Boc-N-Me-Nε-acetyl-Nε-(3-benzyloxycarbonylaminopropyl)-Lys-Tyr (3-tert-Bu)-OMe.

¹H-NMR (CDCl₃): δ 1.08–2.00 (8H, m), 1.37 (9H, s), 1.43 (9H, s), 2.05 (3.H, s), 2.96 (1H, dd, J=6.9, 14.5 Hz), 3.04–3.42 (7H, m), 3.73 (3H, s), 4.30–4.60 (1H, m), 4.76 (1H, q, J=6.3 Hz), 5.09 (2H, s), 5.77 (1H, brs), 6.30–6.50 (1H, m), 6.58–6.82 (2H, m), 6.95 (1H, s), 7.30–7.40 (5H, m).

(5) Synthesis of N-Me-Nε-acetyl-Nε-(3-benzyloxycarbonylaminopropyl)-Lys-Tyr (3-tert-Bu)-OMe To a solution of 1.82 g (2.50 mmol) of Boc-N-Me-Nε-(3-benzyloxycarbonylaminopropyl)-Nε-acetyl-Lys-Tyr (3-tert-Bu)-OMe in 20 ml of methylene chloride was added 10 ml of TFA, and the mixture was stirred at room temperature for 40 minutes. The reaction solution was distilled off under reduced pressure, and the residue was neutralized with saturated aqueous NaHCO₃ solution, extracted with chloroform and the extract was washed with saturated aqueous sodium chloride solution. The organic layer was dried over magnesium sulfate, and then the solvent was distilled off under reduced pressure to give 1.56 g (99%) of N-Me-Nε-acetyl-Nε-(3-benzyloxycarbonylaminopropyl)-Lys-Tyr (3-tert-Bu)-OMe.

¹H-NMR (CDCl₃): δ 0.74–1.82 (8H, m), 1.38 and 1.39 (total 9H, s), 2.02 and 2.07 (total 3H, s), 2.35 and 2.37 (total 3H, s), 2.60–3.40 (9H, m), 3.76 and 3.77 (total 3H, s), 4.78–5.00 (3/2H, m), 5.12 (2H, s), 5.52–5.60 (1/2H, m), 6.60–7.04 (7/2H, m), 7.30–7.46 (5H, m), 7.67 (1/2H, m).

(6) Synthesis of Boc-Phe (4-F)-N-Me-Nε-acetyl-Nε-(3-benzyloxycarbonylaminopropyl)-Lys-Tyr (3-tert-Bu)-OMe To a solution of 1.50 g (2.39 mmol) of N-Me-Nε-acetyl-Nε-(3-benzyloxycarbonylaminopropyl)-Lys-Tyr (3-tert-Bu)-OMe and 811 mg (2.87 mmol) of Boc-Phe (4-F)-OH in 16 ml of THF were added 794 mg (3.11 mmol) of CMPI and 0.733 ml (5.26 mmol) of TEA with ice cooling, and the mixture was stirred at room temperature for 14 hours. The reaction solution was combined with water and extracted with ethyl acetate, and then the extract was washed with saturated aqueous sodium chloride solution. The organic layer was dried over magnesium sulfate, and then the solvent was distilled off under reduced pressure, and the residue was purified by silica gel column chromatography (developing solvent; ethyl acetate:hexane=2:1) to give 1.96 g (92%) of Boc-Phe (4-F)-N-Me-Nε-acetyl-Nε-(3-benzyloxycarbonylaminopropyl)-Lys-Tyr (3-tert-Bu)-OMe.

¹H-NMR (CDCl₃): δ 1.00–1.90 (8H, m), 1.35, 1.36 and 1.38 (total 18H, s), 2.04 (3H, s), 2.20 and 2.55 (total 3H, s), 2.66–3.42 (10H, m), 3.70 and 3.76 (total 3H, s), 4.60–5.04 (3H, m), 5.10 (2H, s), 5.20–6.24 (3H, m), 6.58–7.20 (7H, m), 7.30–7.44 (5H, m).

(7) Synthesis of Boc-Phe (4-F)-N-Me-Nε-acetyl-Nε-(3-aminopropyl)-Lys-Tyr (3-tert-Bu)-OH To a solution of 1.89 g (2.12 mmol) of Boc-Phe (4-F)-N-Me-Nε-acetyl-Nε-(3-benzyloxycarbonylaminopropyl)-Lys-Tyr (3-tert-Bu)-OMe in 20 ml of dioxane was added 2 ml of 2N aqueous sodium hydroxide solution, and the mixture was stirred at room temperature for 100 minutes. The reaction solution was combined with 10% aqueous citric acid solution with ice cooling, extracted with chloroform and the extract was washed with saturated aqueous sodium chloride solution. The organic layer was dried over magnesium sulfate, and then the solvent was distilled off under reduced pressure to give 1.87 g (100%) of Boc-Phe (4-F)-N-Me-Nε-acetyl-Nε-(3-benzyloxycarbonylaminopropyl)-Lys-Tyr (3-tert-Bu)-OH.

To a solution of 1.82 g (2.08 mmol) of Boc-Phe (4-F)-N-Me-Nε-acetyl-Nε-(3-benzyloxycarbonylaminopropyl)-Lys-Tyr (3-tert-Bu)-OH in 20 ml of methanol was added 200 mg of 10% palladium on carbon, and the mixture was stirred overnight at room temperature under a hydrogen atmosphere. After filtration, the filtrate was concentrated under reduced pressure to give 1.32 g (85%) of Boc-Phe (4-F)-N-Me-Nε-acetyl-Nε-(3-aminopropyl)-Lys-Tyr (3-tert-Bu)-OH.

¹H-NMR (DMSO-d): δ 1.00–2.00 (8H, m), 1.28 and 1.38 (total 18H, s), 1.96 (3H, s), 2.30–3.50 (9H, m), 4.00–5.00 (3H, m), 6.54–6.98 (3H, m), 7.00–7.30 (4H, m), 7.30–7.44 (1H, m), 8.96 (1H, d, J=5.3 Hz).

(8) Synthesis of (2S-(2S,13S))-N-(8-acetyl-2-(3-tert-butyl-4-hydroxyphenylmethyl)-3,14-dioxo-1,4,8-triazacyclotetradec-13-yl)-2-tert-butoxycarbonylamino-3-(4-fluorophenyl)-N-methylpropionamide To a mixed solution of 1.10 g (1.48 mmol) of Boc-Phe (4-F)-N-Me-Nε-acetyl-Nε-(3-aminopropyl)-Lys-Tyr (3-tert-Bu)-OH in 75 ml of DMF and 75 ml of pyridine was added 1.96 g (4.44 mmol) of BOP reagent, and the mixture was stirred at room temperature for 18 hours. The reaction solution was concentrated under reduced pressure, combined with water and extracted with ethyl acetate, and then the extract was successively washed with 10% aqueous citric acid solution and saturated aqueous sodium chloride solution. The organic layer was dried over magnesium sulfate, and then the solvent was distilled off under reduced pressure, and the residue was purified by silica gel column chromatography (developing solvent; methylene chloride:methanol:aqueous ammonia=20:1:0.05) to give 0.59 g (55%) of 2S-(2S,13S))-N-(8-acetyl-2-(3-tert-butyl-4-hydroxyphenylmethyl)-3,14-dioxo-1,4,8-triazacyclotetradec-13-yl)-2-tert-butoxycarbonylamino-3-(4-fluorophenyl)-N-methylpropionamide.

(9) Synthesis of (2S-(2S,13S))-N-(8-acetyl-2-(3-tert-butyl-4-hydroxyphenylmethyl)-3,14-dioxo-1,4,8-triazacyclotetradec-13-yl)-2-amino-3-(4-fluorophenyl)-N-methylpropionamide To a solution of 0.55 g (0.757 mmol) of (2S-(2S,13S))-N-(8-acetyl-2-(3-tert-butyl-4-hydroxyphenylmethyl)-3,14-dioxo-1,4,8-triazacyclotetradec-13-yl)-2-tert-butoxycarbonylamino-3-(4-fluorophenyl)-N-methylpropionamide in 7 ml of methylene chloride was added 3 ml of TFA, and the mixture was stirred at room temperature for 55 minutes. The reaction solution was distilled off under reduced pressure, and the residue was neutralized with saturated aqueous $NaHCO_3$ solution, extracted with methylene chloride and the extract was washed with saturated aqueous sodium chloride solution. The organic layer was dried over magnesium sulfate, and then the solvent was distilled off under reduced pressure, and the residue was purified by silica gel column chromatography (developing solvent; methylene chloride:methanol:aqueous ammonia=15:1:0.1) to give 0.43 g (90%) of the title compound.

FAB-MS ($M^+$+1): 626. $^1$H-NMR (DMSO-d6-$CDCl_3$): δ 0.7–1.8 (16H, m), 1.29 and 1.30 (total 9H, s), 1.9–2.0 (3H, m), 2.4–3.4 (10H, m), 2.62 and 2.64 (3H, s), 3.70 (0.5H, m), 4.0–4.4 (2H, m), 4.92 (0.5H, d, J=9.2 Hz), 6.5–7.2 (8H, m), 7.8–8.1 (1.5H, m), 9.0–9.1 (1.5H, m).

Example 9

Synthesis of (2S-(2S,13S))-2-amino-N-(2-(3-tert-butyl-4-hydroxyphenylmethyl)-9,N-dimethyl-1,4,9-triaza-3,8,14-trioxocyclotetradec-13-yl)-3-(4-fluorophenyl)propionamide (1) Synthesis of Boc-N-Me-Orn (Me) (Z)-OH To a solution of 3.00 g (8.19 mmol) of Boc-Orn (Z)-OH in 82 ml of THF were added 1.31 g (32.8 mmol) of 60% sodium hydride and 4.08 ml (65.5 mmol) of methyl iodide with ice cooling, and the mixture was stirred at room temperature for 16 hours. The reaction solution was combined with water with ice cooling, and washed with hexane. The aqueous layer was combined with 10% aqueous citric acid solution, extracted with ethyl acetate and the extract was washed with saturated aqueous sodium chloride solution. The organic layer was dried over magnesium sulfate, and then the solvent was distilled off under reduced pressure to give 3.22 g (100%) of Boc-N-Me-Orn (Me) (Z)-OH.

$^1$H-NMR ($CDCl_3$): δ 1.46 (9H, s), 1.50–2.02 (4H, m), 2.70–2.90 (3H, m), 2.92 (3H, s), 3.20–3.46 (2H, m), 4.32–4.80 (1H, m), 5.13 (2H, s), 7.24–7.40 (5H, m).

(2) Synthesis of N-(Boc-N-Me-Nε-Z-ornithyl-3-tert-Bu-tyrosyl)-4-aminobutyric acid benzyl ester To a solution of 2.39 g (5.80 mmol) of N-(3-tert-Bu-tyrosyl)-4-aminobutyric acid benzyl ester and 2.51 g (6.38 mmol) of Boc-N-Me-Orn (Z)-OH in 29 ml of DMF were added 784 mg (5.80 mmol) of HOBt, 0.729 ml (6.38 mmol) of NMM and 1.22 g (6.38 mmol) of WSCI with ice cooling, and the mixture was stirred at room temperature for 140 minutes. The reaction solution was combined with water and extracted with ethyl acetate, and then the extract was successively washed with 10% aqueous citric acid solution, saturated aqueous $NaHCO_3$ solution and saturated aqueous sodium chloride solution. The organic layer was dried over magnesium sulfate, and then the solvent was distilled off under reduced pressure, and the residue was purified by silica gel column chromatography (developing solvent; ethyl acetate:hexane=1:1) to give 3.91 g (86%) of N-(Boc-N-Me-Nε-Z-ornithyl-3-tert-Bu-tyrosyl)-4-aminobutyric acid benzyl ester.

$^1$H-NMR ($CDCl_3$): δ 1.36 (9H, s), 1.45 (9H, s), 1.50–1.90 (4H, m), 2.26 (2H, t, J=7.3 Hz), 2.47 and 2.58 (total 3H, s), 2.88 (3H, s), 2.95 (2H, d, J=7.3 Hz), 3.10–3.44 (4H, m), 4.42–4.60 (2H, m), 5.09 (2H, s), 5.12 (2H, s), 5.30–5.50 (1H, m), 5.90–6.10 (1H, m), 6.54 (1H, d, J=7.9 Hz), 6.83 (1H, d, J=7.9 Hz), 7.04 (1H, s), 7.24–7.40 (10H, m).

(3) Synthesis of N-(N-Me-Nε-Z-ornithyl-3-tert-Bu-tyrosyl)-4-aminobutyric acid benzyl ester To a solution of 3.81 g (4.84 mmol) of N-(Boc-N-Me-Nε-Z-ornithyl-3-tert-Bu-tyrosyl)-4-aminobutyric acid benzyl ester in 40 ml of methylene chloride was added 10 ml of TFA, and the mixture was stirred at room temperature for 40 minutes. The reaction solution was distilled off under reduced pressure, and the residue was neutralized with saturated aqueous $NaHCO_3$ solution, extracted with chloroform and the extract was washed with saturated aqueous sodium chloride solution. The organic layer was dried over magnesium sulfate, and then the solvent was distilled off under reduced pressure to give 3.26 g (98%) of N-(N-Me-Nε-Z-ornithyl-3-tert-Bu-tyrosyl)-4-aminobutyric acid benzyl ester.

$^1$H-NMR ($CDCl_3$): δ 1.06–1.40 (2H, m), 1.37 (9H, s), 1.78 (2H, tt, J=6.9, 7.3 Hz), 2.27 (3H, s), 2.32 (2H, t, J=7.3 Hz), 2.76–2.92 (5H, m), 2.98–3.30 (3H, m), 3.225 (2H, q, J=6.9 Hz), 4.34–4.56 (1H, m), 5.10 and 5.14 (total 4H, s), 6.30–6.88 (3 h, m), 7.02 (1H, d, J=2.6 Hz), 7.30–7.62 (11H, m).

(4) Synthesis of N-(Boc-4-fluorophenylalanyl-N-Me-Nε-Z-ornithyl-3-tert-Bu-tyrosyl)-4-aminobutyric acid benzyl ester To a solution of 3.10 g (4.51 mmol) of N-(N-Me-Nε-Z-ornithyl-3-tert-Bu-tyrosyl)-4-aminobutyric acid benzyl ester and 1.41 g (4.96 mmol) of Boc-Phe (4-F)-OH in 45 ml of THF were added 1.38 g (5.41 mmol) of CMPI and 1.38 ml (9.92 mmol) of TEA with ice cooling, and the mixture was stirred at room temperature for 14 hours. The reaction solution was combined with water and extracted with ethyl acetate, and then the extract was washed with saturated aqueous sodium chloride solution. The organic layer was dried over magnesium sulfate, and then the solvent was distilled off under reduced pressure, and the residue was purified by silica gel column chromatography (developing solvent; ethyl acetate:hexane=2:1) to give 4.20 g (98%) of N-(Boc-4-fluorophenylalanyl-N-Me-Nε-Z-ornithyl-3-tert-Bu-tyrosyl)-4-aminobutyric acid benzyl ester.

$^1$H-NMR ($CDCl_3$): δ 1.20–1.50 (2H, m), 1.34 and 1.38 (total 18H, s), 1.60–1.84 (4H, m), 2.04–3.40 (16H, m), 4.30–5.06 (5/2H, m), 5.08 and 5.11 (total 4H, s), 5.29 (1/2H, d, J=6.6 Hz), 5.60–6.30 (2H, m), 6.40–7.20 (7H, m), 7.24–7.42 (21/2H, m), 7.68–7.76 (1/2H, m).

(5) (2S-(2S,13S))-2-tert-butoxycarbonylamino-N-(2-(3-tert-butyl-4-hydroxyphenylmethyl)-9-methyl-1,4,9-triaza-3,8,14-trioxocyclotetradec-13-yl)-3-(4-fluorophenyl)-N-methylpropionamide To a solution of 2.80 g (2.68 mmol) of N-(Boc-4-fluorophenylalanyl-N-Me-Nε-Z-ornithyl-3-tert-Bu-tyrosyl)-4- aminobutyric acid benzyl ester in 40 ml of methanol was added 0.52 g of palladium hydroxide on carbon, and the mixture was stirred at room temperature for 5 hours under a hydrogen atmosphere. The reaction solution was filtered, and the filtrate was concentrated under reduced pressure, and a mixed solution of 2.27 g of the residue in 135 ml of DMF and 135 ml of pyridine was stirred with 3.56 g (8.04 mmol) of BOP reagent at room temperature for 12 hours. The reaction solution was concentrated under reduced pressure, combined with water and extracted with ethyl acetate, and then the extract was successively washed with 10% aqueous citric acid solution and saturated aqueous sodium chloride solution. The organic layer was dried over magnesium sulfate, and then the solvent was distilled off under reduced pressure, and the residue was purified by silica gel column chromatography (developing solvent; methylene chloride: methanol:aqueous ammonia=20:1:0.1) to give 1.14 g (60%) of (2S-(2S,13S))-2-tert-butoxycarbonylamino-N-(2-(3-tert-butyl-4-hydroxyphenylmethyl)-9-methyl-1,4,9-triaza-3,8,14-trioxocyclotetradec-13-yl)-3-(4-fluorophenyl)-N-methylpropionamide.

(6) Synthesis of (2S-(2S,13S))-2-amino-N-(2-(3-tert-butyl-4-hydroxyphenylmethyl)-9-methyl-1,4,9-triaza-3,8,14-trioxocyclotetradec-13-yl)-3-(4-fluorophenyl)-N-methylpropionamide To a solution of 1.10 g (1.54 mmol) of (2S-(2S,13S))-2-tert-butoxycarbonylamino-N-(2-(3-tert-butyl-4-hydroxyphenylmethyl)-9-methyl-1,4,9-triaza-3,8,14-trioxocyclotetradec-13-yl)-3-(4-fluorophenyl)-N-methylpropionamide in 9 ml of methylene chloride was added 3 ml of TFA, and the mixture was stirred at room temperature for 1 hour. The reaction solution was distilled off under reduced pressure, and the residue was neutralized with saturated aqueous NaHCO$_3$ solution, extracted with methylene chloride and the extract was washed with saturated aqueous sodium chloride solution. The organic layer was dried over magnesium sulfate, and then the solvent was distilled off under reduced pressure, and the residue was purified by silica gel column chromatography (developing solvent; methylene chloride:methanol:aqueous ammonia=13:1:0.1) to give 609 mg (65%) of the title compound.

FAB-MS (M$^+$+1): 612. $^1$H-NMR (DMSO-d6-CDCl$_3$): δ 0.8–2.0 (6H, m), 1.29 (9H, s), 2.0–3.4 (12H, m), 3.6–4.5 (3.5H, m), 4.9–5.1 (0.75H, m), 5.4–5.7 (0.75H, m), 6.6–7.3 (10H, m), 7.6–7.8 (1H, m), 8.0–8.3 (1H, m), 8.9–9.2 (2H, m).

Example 10

Synthesis of (2S-(2S,13S))-2-amino-N-(2-(3-tert-butyl-4-hydroxyphenylmethyl)-1,4,8-triaza-3,7,14-trioxocyclotetradec-13-yl)-3-phenyl-N-methylpropionamide (1) Synthesis of H-Tyr (3-tert-Bu)-β-Ala-O-tert-Bu To a mixed solution of 3.5 g (13.9 mmol) of H-Tyr (3-tert-Bu)-OMe and 2.21 g (20.9 mmol) of sodium carbonate in 25 ml of 1,4-dioxane and 25 ml of water was added 2.09 ml (14.6 mmol) of benzyloxycarbonyl chloride with ice cooling, and the mixture was stirred at room temperature for 2 hours. The reaction solution was combined with water, extracted with ethyl ether, and then the extract was washed with saturated aqueous sodium chloride solution. The organic layer was dried over anhydrous magnesium sulfate, and then the solvent was distilled off under reduced pressure, and the resulting crude Z-Tyr (3-tert-Bu)-OMe in 20 ml of 1,4-dioxane was stirred with a solution of 1.05 g (26.3 mmol) of sodium hydroxide in 10 ml of water at room temperature for 40 minutes. The reaction solution was washed with ethyl ether, and then the aqueous layer was acidified with concentrated hydrochloric acid and extracted with methylene chloride. The extract was dried over anhydrous magnesium sulfate, and then concentrated under reduced pressure, and 1.88 g (13.9 mmol) of HOBt, 1.6 ml (13.9 mmol) of NMM and 2.93 g (15.3 mmol) of WSCI were added to a solution of the resulting crude Z-Tyr (3-tert-Bu)-OH and 2.78 g (15.3 mmol) of H-β-Ala-O-tert-Bu hydrochloride in 40 ml of DMF with ice cooling, and the mixture was stirred overnight at room temperature. The reaction solution was combined with water, 10% aqueous citric acid solution and extracted with ethyl acetate, and then the extract was successively washed with saturated aqueous NaHCO$_3$ solution and saturated aqueous sodium chloride solution. The extract was dried over magnesium sulfate, and then the solvent was distilled off under reduced pressure, and a solution of the resulting crude Z-Tyr (3-tert-Bu)-β-Ala-O-tert-Bu in 70 ml of methanol was stirred with 1.0 g of 20% palladium hydroxide on carbon for 1 hour under a hydrogen atmosphere. The reaction solution was filtered, and the filtrate was concentrated under reduced pressure to give 4.70 g (93%) of the title compound.

$^1$H-NMR (CDCl$_3$): δ 1.39 (9H, s), 1.45 (9H, s), 2.44 (2H, t, J=6.3 Hz), 2.57 (1H, dd, J=9.4, 13.9 Hz), 3.17 (1H, dd, J=4.0, 13.9 Hz), 3.47–3.56 (3H, m), 6.64 (1H, d, J=7.9 Hz), 6.90 (1H, dd, J=2.0, 7.9 Hz), 7.08 (1H, d, J=2.0 Hz), 7.67 (1H, brt).

(2) Synthesis of Fmoc-N-Me-Lys (Boc)-Tyr (3-tert-Bu)-β-Ala-O-tert-Bu

To a solution of 3.97 g (10.9 mmol) of H-Tyr (3-tert-Bu)-β-Ala-O-tert-Bu and 5.26 g (10.9 mmol) of Fmoc-N-Me-Lys (Boc)-OH in 40 ml of DMF were added 1.47 g (10.9 mmol) of HOBt, 1.25 ml (10.9 mmol) of NMM and 2.09 g (10.9 mmol) of WSCI with ice cooling, and the mixture was stirred overnight at room temperature. The reaction solution was combined with water and 10% aqueous citric acid solution and extracted with ethyl acetate, and then the extract was successively washed with saturated aqueous NaHCO$_3$ solution and saturated aqueous sodium chloride solution. The organic layer was dried over magnesium sulfate, and then the solvent was distilled off under reduced pressure, and the residue was purified by silica gel column chromatography (using ethyl acetate:n-hexane=1:1 as eluent) to give 8.14 g (90%) of the title compound.

$^1$H-NMR (CDCl$_3$): δ 1.0–1.9 (6H, m), 1.34 (9H, s), 1.42 (9H, s), 1.44 (9H, s), 2.3–2.4 (2H, m), 2.55 (3H, brs), 2.7–2.9 (1H, m), 3.0–3.1 (3H, m), 3.4–3.5 (2H, m), 4.2–4.6 (6H, m), 6.45 (2H, brs), 6.75 (1H, brs), 7.00 (1H, s), 7.3–7.5 (5H, m), 7.58 (2H, d, J=6.3 Hz), 7.79 (2H, d, J=7.6 Hz).

(3) Synthesis of N-Me-Lys (Boc)-Tyr (3-tert-Bu)-β-Ala-O-tert-Bu

To a solution of 6.8 g (8.20 mmol) of Fmoc-N-Me-Lys (Boc)-Tyr (3-tert-Bu)-β-Ala-O-tert-Bu in 15 ml of methylene chloride was added 15 ml of diethylamine, and the mixture was stirred at room temperature for 95 minutes. The reaction solution was distilled off under reduced pressure, and the residue was purified by silica gel column chromatography (using methylene chloride:methanol aqueous ammonia=30:1:0.1 as eluent) to give 4.57 g (91%) of the title compound.

$^1$H-NMR (CDCl$_3$): δ 0.8–0.9 (2H, m), 1.0–1.7 (4H, m), 1.38 (9H, s), 1.44 (9H, s), 1.48 (9H, s), 2.33 (3H, s), 2.43 (2H, t, J=5.9–6.3 Hz), 2.7–3.1 (4H, m), 3.25 (1H, dd, J=4.6, 14.2 Hz), 3.49 (2H, dd, J=5.9–6.3, 11.9–12.2 Hz), 4.5–4.7 (2H, m), 6.7–6.8 (2H, m), 6.86 (1H, d, J=6.6 Hz), 7.03 (1H, s), 7.38 (1H, d, J=7.9 Hz).

(4) Synthesis of Z-Phe-N-Me-Lys (Boc)-Tyr (3-tert-Bu)-β-Ala-O-tert-Bu

To a solution of 4.57 g (7.53 mmol) of N-Me-Lys (Boc)-Tyr (3-tert-Bu)-β-Ala-O-tert-Bu, 2.93 g (9.79 mmol) of Z-Phe-OH and 2.69 g (10.5 mmol) of CMPI in 20 ml of THF was added 3.1 ml (22.6 mmol) of TEA with ice cooling, and the mixture was stirred overnight at room temperature. The reaction solution was combined with water and extracted with ethyl acetate, and then the extract was successively washed with saturated aqueous NaHCO$_3$ solution and saturated aqueous sodium chloride solution. The organic layer was dried over magnesium sulfate, and then the solvent was distilled off under reduced pressure, and the residue was purified by silica gel column chromatography (developing solvent; ethyl acetate:hexane=3:1) to give 6.7 g (quant.) of the title compound.

(5) Synthesis of (2S-(2S,13S))-2-benzyloxycarbonylamino-N-(2-(3-tert-butyl-4-hydroxyphenylmethyl)-1,4,8-triaza-3,7,14-trioxocyclotetradec-13-yl)-3-phenyl-N-methylpropionamide To a solution of 6.7 g (7.53 mmol) of Z-Phe-N-Me-Lys (Boc)-Tyr (3-tert-Bu)-β-Ala-O-tert-Bu in 40 ml of methylene chloride was added 40 ml of TFA, and the mixture was stirred at room temperature for 70 minutes. The reaction solution was concentrated under reduced pressure, and the residue was combined with toluene, and the solvent was distilled off under reduced pressure. A mixed solution of the resulting crude Z-Phe-N-Me-Lys-Tyr (3-tert-Bu)-β-Ala-OH in 380 ml of DMF and 380 ml of pyridine was stirred with 9.99 g (22.6 mmol) of BOP reagent overnight at room temperature. The reaction solution was concentrated under reduced pressure, and the residue was purified by silica gel column chromatography (developing solvent; chloroform methanol:aqueous ammonia=80-20:1:0.05). The residue was dissolved in ethyl acetate, and successively washed with 10% aqueous citric acid solution, saturated aqueous NaHCO$_3$ solution and saturated aqueous sodium chloride solution, and dried over anhydrous magnesium sulfate, and then the solvent was distilled off under reduced pressure to give 2.6 g (48%) of the title compound.

(6) Synthesis of (2S-(2S,13S))-2-amino-N-(2-(3-tert-butyl-4-hydroxyphenylmethyl)-1,4,8-triaza-3,7,14-trioxocyclotetradec-13-yl)-3-phenyl-N-methylpropionamide To a solution of 1.25 g (1.79 mmol) of (2S-(2S,13S))-2-benzyloxycarbonylamino-N-(2-(3-tert-butyl-4-hydroxyphenylmethyl)-1,4,8-triaza-3,7,14-trioxocyclotetradec-13-yl)-3-phenyl-N-methylpropionamide in 35 ml of methanol was added 0.55 g of 10% palladium hydroxide on carbon, and the mixture was stirred for 2.5 hours under a hydrogen atmosphere. The reaction solution was filtered, and the filtrate was concentrated under reduced pressure, and the residue was purified by silica gel column chromatography (developing solvent; chloroform:methanol:aqueous ammonia=20:1:0.1) to give 1.48 g (73%) of the title compound.

FAB-MS (M$^+$+1): 580

$^1$H-NMR (DMSO-d6-CDCl$_3$): δ 0.60–2.0 (6H, m), 1.29 (9H, s), 2.1–2.3 (2H, m), 2.5–2.9 (4H, m), 2.66 and 2.60 (3H, s), 3.1–3.3 (2H, m), 3.5–3.6 (2H, m), 3.71 and 3.92 (1H, t, J=6.3 Hz), 4.18 and 4.94 (1H, d, J=11.9 Hz), 4.4–4.6 (1H, m), 6.60–6.64 (1H, m), 6.72 and 6.75 (1H, dd, J=1.9, 8.0 Hz), 6.86 and 6.93 (1H, d, J=1.9 Hz), 7.05–7.29 (5H, m), 7.6–7.8 (2H, m), 8.09 and 8.39 (1H, d, J=8.8–9.4), 8.9–9.1 (1H, s).

In the following test examples, representative compounds of the present invention were evaluated for motilin receptor antagonist activity by pharmacological tests in order to demonstrate the utility of compounds of the present invention.

Test Example 1

Motilin Receptor Binding Test

Motilin receptor binding activities of compounds of the present invention were tested as follows [Vantrappen et al., Regul. Peptides, 15, 143 (1986)].

A protein solution was prepared by homogenizing the duodenum isolated from a killed rabbit in 50 mM Tris after stripping the mucosa. The protein solution was incubated with 25 pM $^{125}$I motilin for 2 hours at 25° C., and then the radioactivity bound to the protein was measured with a γ-counter (COBRA II™, model 5005, Packard). The difference between the radioactivity of the protein solution incubated alone and the radioactivity of the protein solution incubated with a large excess of motilin (10$^{-7}$ M) was recorded as specific binding of motilin to motilin receptors.

The concentration required to inhibit 50% of the specific binding of motilin to motilin receptors (IC$_{50}$, nM) was determined for the compounds synthesized in Examples 1–10 above. As a comparative example, the IC$_{50}$ of the compound of formula (5) below, i.e. a cyclic peptide derivative having motilin antagonist activity (the compound described in JP-A-7-138284) was also determined. The results are shown in Table B-1.

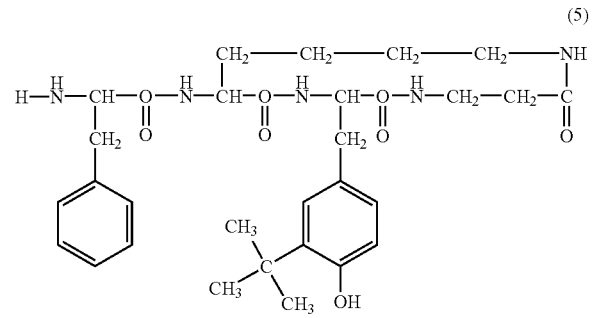

(5)

Test Example 2

Effect on the Contraction of a Sample of the Longitudinal Duodenal Muscle Extracted from Rabbit The effect of compounds of the present invention on motilin-induced contraction of a sample of the longitudinal muscle of the duodenum extracted from a rabbit was tested as follows.

A duodenal specimen (5×15 mm) extracted from a killed rabbit was suspended in the direction of the longitudinal muscle in an incubator at 28° C. filled with Krebs solution (10 ml organ bath). A mixed gas (95% $O_2$, 5% $CO_2$) was continuously passed through the Krebs solution and the contraction of the duodenal specimen was isotonically recorded (under a load of 1 g) via an isotonic transducer (ME-3407, ME Commercial, Tokyo, Japan). The extent of contraction of the duodenal specimen was expressed as a percentage to the contraction induced by acetylcholine at a concentration of $10^{-4}$ M.

The effect of the compounds synthesized in Examples 1–8 and 10 on the concentration-dependent contraction induced by motilin added into the incubator was determined to calculate $pA_2$ (see "Drug receptors" edited by Takayanagi, published by Nanzando). The results are shown in Table B-1. As a comparative example, the results of the compound of formula (5) are also shown.

TABLE B-1

| Example No. | Motilin receptor binding test $IC_{50}$ (nM) | Contraction inhibition test $pA_2$ |
| --- | --- | --- |
| 1 | 1.2 | 9.0 |
| 2 | 1.4 | 8.9 |
| 3 | 0.52 | 8.2 |
| 4 | 0.78 | 9.0 |
| 5 | 1.4 | 9.9 |
| 6 | 0.87 | 8.5 |
| 7 | 4.5 | 8.0 |
| 8 | 0.84 | 8.2 |
| 9 | 5.3 | |
| 10 | 2.2 | 7.9 |
| Comparative example | 10 | 7.2 |

Table B-1 shows that the compounds of the present invention have excellent motilin receptor antagonist activity as compared with the compound of the comparative example.

INDUSTRIAL APPLICABILITY

Compounds of the present invention have motilin receptor antagonist activity or the like and are useful as pharmaceuticals such as pharmaceuticals for treating irritable bowel syndrome.

The invention claimed is:

1. A compound of general formula (1):

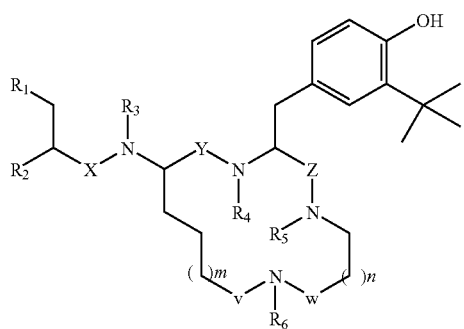

wherein
$R_1$ represents an optionally substituted phenyl group or an optionally substituted heterocycle;
$R_2$ represents a hydrogen atom or an optionally substituted amino group;
$R_3$ represents a hydrogen atom, a methyl group or an ethyl group;
$R_4$ represents a hydrogen atom, a methyl group or an ethyl group;
$R_5$ represents a hydrogen atom, a methyl group or an ethyl group;
$R_6$ represents a hydrogen atom, a methyl group, an ethyl group or —CO—$R_7$;
$R_7$ represents a hydrogen atom or a straight or branched alkyl group having 1–3 carbon atoms;
V represents a carbonyl group or a methylene group;
W represents a carbonyl group or a methylene group:
X represents a carbonyl group or a methylene group;
Y represents a carbonyl group or a methylene group;
Z represents a carbonyl group or a methylene group;
m represents a number of 0–2; and
n represents a number of 0–3;
except for the case where $R_1$ represents a phenyl group, $R_2$ represents an amino group, all of $R_3$, $R_4$, $R_5$ and $R_6$ represent a hydrogen atom, V represents a methylene group, all of W, X, Y and Z represent a carbonyl group, and both m and n represent 1; or
a hydrate or a pharmaceutically acceptable salt thereof.

2. The compound of general formula (1) of claim 1 wherein X is a methylene group when $R_1$ is a phenyl group and $R_3$ is a hydrogen atom, or a hydrate or a pharmaceutically acceptable salt thereof.

3. The compound of general formula (1) of claim 1, wherein $R_1$ is a phenyl group or a halogen-substituted phenyl group, or a hydrate or a pharmaceutically acceptable salt thereof.

4. The compound of general formula (1) of any one of claim 1, wherein $R_2$ is an amino group, or a hydrate or a pharmaceutically acceptable salt thereof.

5. The compound of general formula (1) of claim 1, wherein $R_3$ is a hydrogen atom or a methyl group, or a hydrate or a pharmaceutically acceptable salt thereof.

6. The compound of general formula (1) of claim 1, wherein $R_4$ is a hydrogen atom or a methyl group, or a hydrate or a pharmaceutically acceptable salt thereof.

7. The compound of general formula (1) of claim 1, wherein $R_5$ is a hydrogen atom or a methyl group, or a hydrate or a pharmaceutically acceptable salt thereof.

8. The compound of general formula (1) of claim 1, wherein $R_6$ is a hydrogen atom, a methyl group or an acetyl group, or a hydrate or a pharmaceutically acceptable salt thereof.

9. The compound of general formula (1) of claim 1, wherein V is a methylene group, or a hydrate or a pharmaceutically acceptable salt thereof.

10. The compound of general formula (1) of claim 1, wherein Y is a carbonyl group, or a hydrate or a pharmaceutically acceptable salt thereof.

11. The compound of general formula (1) of claim 1, wherein Z is a carbonyl group, or a hydrate or a pharmaceutically acceptable salt thereof.

12. The compound of general formula (1) of claim 1 wherein $R_1$ is a phenyl group or a halogen-substituted phenyl group, $R_2$ is an amino group, $R_3$ is a hydrogen atom or a methyl group, $R_4$ is a hydrogen atom or a methyl group, $R_5$ is a hydrogen atom or a methyl group, $R_6$ is a hydrogen atom, a methyl group or an acetyl group, V is a methylene group, W is a carbonyl group or a methylene group, X is a carbonyl group or a methylene group, Y is a carbonyl group and Z is a carbonyl group, or a hydrate or a pharmaceutically acceptable salt thereof.

13. The compound of claim 1 selected from the group consisting of (2S-(2S,13S))-2-amino-N-(2-(3-tert-butyl-4-hydroxyphenylmethyl)-1,4,8-triaza-3,7,14-trioxocyclotetradec-13-yl)-3-(4-fluorophenyl)-N-methylpropionamide, (2S-(2S,13S))-2-amino-N-(2-(3-tert-butyl-4-hydroxyphenylmethyl)-1-methyl-1,4,8-triaza-3,7,14-trioxocyclotetradec-13-yl)-3-(4-fluorophenyl)-N-methylpropionamide, (2S-(2S,12S))-2-amino-N-(2-(3-tert-butyl-4-hydroxyphenylmethyl)-1,4,8-triaza-3,7,13-trioxocyclotridec-12-yl)-3-(4-fluorophenyl)-N-methylpropionamide, (2S-(2S,13S))-2-amino-N-(2-(3-tert-butyl-4-hydroxyphenylmethyl)-4-methyl-1,4,8-triaza-3,7,14-trioxocyclotetradec-13-yl)-3-(4-fluorophenyl)-N-methylpropionamide, (2S-(2S,13S))-2-amino-N-(2-(3-tert-butyl-4-hydroxyphenylmethyl)-8-methyl-1,4,8-triaza-3,7,14-trioxocyclotetradec-13-yl)-3-(4-fluorophenyl)-N-methylpropionamide, (2S-(2S,14S))-2-amino-N-(2-(3-tert-butyl-4-hydroxyphenylmethyl)-1,4,9-triaza-3,8,15-trioxocyclopentadec-14-yl)-3-(4-fluorophenyl)-N-methylpropionamide, (2S,14S)-13-(2S-2-amino-3-(4-fluorophenyl)propylamino)-2-(3-tert-butyl-4-hydroxyphenylmethyl)-1,4,8-triaza-3,7,14-trioxocyclotetradecane, (2S-(2S,13S))-N-(8-acetyl-2-(3-tert-butyl-4-hydroxyphenylmethyl)-N-methyl-1,4,8-triaza-3,14-dioxocyclotetradec-13-yl)-2-amino-3-(4-fluorophenyl) propionamide, (2S-(2S,13S))-2-amino-N-(2-(3-tert-butyl-4-hydroxyphenylmethyl)-9,N-dimethyl-1,4,9-triaza-3,8,14-trioxocyclotetradec-13-yl)-3-(4-fluorophenyl) propionamide, (2S-(2S,13S))-2-amino-N-(2-(3-tert-butyl-4-hydroxyphenylmethyl)-1,4,8-triaza-3,7,14-trioxocyclotetradec-13-yl)-3-phenyl-N-methylpropionamide, or a hydrate or a pharmaceutically acceptable salt thereof.

14. A pharmaceutical comprising the compound of claim 1, or a hydrate or a pharmaceutically acceptable salt thereof as an active ingredient.

15. A motilin receptor antagonist comprising the compound of claim 1, or a hydrate or a pharmaceutically acceptable salt thereof.

16. A gastrointestinal motility inhibitor comprising the compound of claim 1, or a hydrate or a pharmaceutically acceptable salt thereof as an active ingredient.

17. A pharmaceutical for treating hypermotilinemia comprising the compound of claim 1, or a hydrate or a pharmaceutically acceptable salt thereof as an active ingredient.

18. A compound of general formula (2):

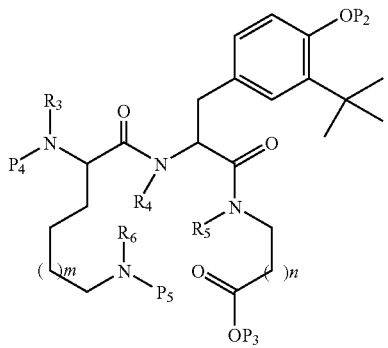

(2)

wherein
$R_3$ represents a hydrogen atom, a methyl group or an ethyl group;
$R_4$ represents a hydrogen atom, a methyl group or an ethyl group;
$R_5$ represents a hydrogen atom, a methyl group or an ethyl group;
$R_6$ represents a hydrogen atom, a methyl group, an ethyl group or —CO—$R_7$;

m represents a number of 0–2;
n represents a number of 0–3;
$P_2$ represents a hydrogen atom or a protective group for a phenolic hydroxyl group;
$P_3$ represents a hydrogen atom or a protective group for a carboxyl group;
$P_4$ represents a hydrogen atom or a protective group for an amino group; and
$P_5$ represents a hydrogen atom or a protective group for an amino group; or
a hydrate or a pharmaceutically acceptable salt thereof.

19. A compound of general formula (3):

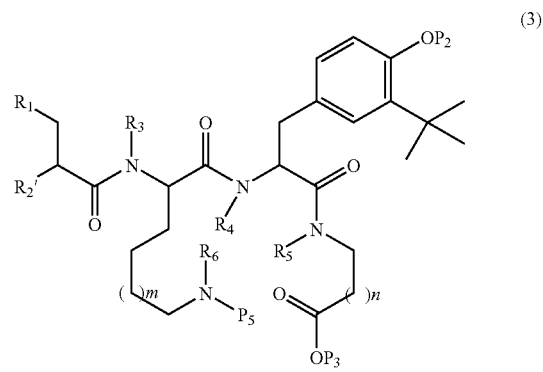

(3)

wherein
$R_1$ represents an optionally substituted phenyl group or an optionally substituted heterocycle;
$R_3$ represents a hydrogen atom, a methyl group or an ethyl group;
$R_4$ represents a hydrogen atom, a methyl group or an ethyl group;
$R_5$ represents a hydrogen atom, a methyl group or an ethyl group;
m represents a number of 0–2;
n represents a number of 0–3;
$P_2$ represents a hydrogen atom or a protective group for a phenolic hydroxyl group;
$P_3$ represents a hydrogen atom or a protective group for a carboxyl group;
$P_5$ represents a hydrogen atom or a protective group for an amino group; and
$R_2'$ represents a hydrogen atom or an optionally substituted protected amino group; or
a hydrate or a pharmaceutically acceptable salt thereof.

20. A compound of general formula (4):

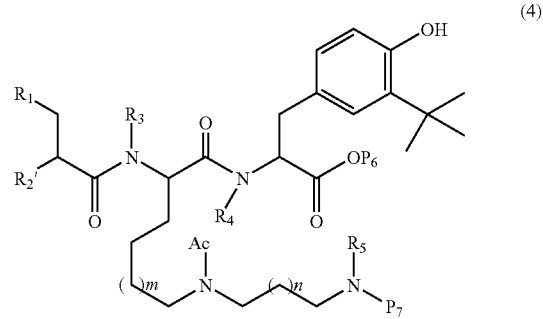

(4)

wherein $R_1$ represents an optionally substituted phenyl group or an optionally substituted heterocycle;

$R_3$ represents a hydrogen atom, a methyl group or an ethyl group;

$R_4$ represents a hydrogen atom, a methyl group or an ethyl group;

$R_5$ represents a hydrogen atom, a methyl group or an ethyl group;

$R_2'$ represents a hydrogen atom or an optionally substituted protected amino group;

m represents a number of 0–2;

n represents a number of 0–3;

$P_6$ represents a hydrogen atom or a protective group for a carboxyl group; and $P_7$ represents a hydrogen atom or a protective group for an amino group; or a hydrate or a pharmaceutically acceptable salt thereof.

21. A method for treating hypermotilinemia comprising the step of administering a therapeutically effective amount of the compound of claim 1, or a hydrate or a pharmaceutically acceptable salt thereof to a patient in need of such treatment.

* * * * *